(12) United States Patent
Dewaele et al.

(10) Patent No.: US 8,882,716 B2
(45) Date of Patent: Nov. 11, 2014

(54) CAPILLARY TUBE ASSEMBLY

(75) Inventors: Frank Dewaele, De Pinte (BE); Alain Kalmar, Ghent (BE); Bart Blanckaert, Eeklo (BE); Cyriel Mabilde, Oudenaarde (BE)

(73) Assignee: Steerable Instruments BVBA, Eeklo (BE)

( * ) Notice: Subject to any disclaimer, the term of this patent is extended or adjusted under 35 U.S.C. 154(b) by 0 days.

(21) Appl. No.: 13/810,427

(22) PCT Filed: Jul. 26, 2011

(86) PCT No.: PCT/EP2011/062810
§ 371 (c)(1),
(2), (4) Date: Jan. 15, 2013

(87) PCT Pub. No.: WO2012/013662
PCT Pub. Date: Feb. 2, 2012

(65) Prior Publication Data
US 2013/0131610 A1 May 23, 2013
US 2014/0005613 A9 Jan. 2, 2014

Related U.S. Application Data

(60) Provisional application No. 61/367,795, filed on Jul. 26, 2010, provisional application No. 61/434,676, filed on Jan. 20, 2011.

(30) Foreign Application Priority Data

Jul. 26, 2010 (EP) .................................. 10170794
Jan. 20, 2011 (EP) .................................. 11151530

(51) Int. Cl.
*A61M 5/00* (2006.01)
(Continued)

(52) U.S. Cl.
CPC ........... *A61M 25/003* (2013.01); *A61M 25/002* (2013.01); *A61B 5/02152* (2013.01);
(Continued)

(58) Field of Classification Search
USPC ........... 604/93, 158, 164, 167, 244, 245, 246, 604/264, 280, 283, 284, 523–525, 905
See application file for complete search history.

(56) References Cited

U.S. PATENT DOCUMENTS 3,185,151 A * 5/1965 Czorny ......................... 604/163
(Continued)

FOREIGN PATENT DOCUMENTS

DE 3206381 A1 9/1983
(Continued)

OTHER PUBLICATIONS

International Preliminary Report on Patentability dated Nov. 23, 2012 issued to international priority application No. PCT/EP2011/062810.
(Continued)

*Primary Examiner* — Kevin C Sirmons
*Assistant Examiner* — William Carpenter
(74) *Attorney, Agent, or Firm* — Knobbe, Martens, Olson & Bear LLP

(57) ABSTRACT

The present invention relates to a device comprising a capillary tube assembly (100) having a proximal (20) end and a distal (30) end, comprising: a think walled capillary tube shaft (10) disposed with a capillary lumen (12) extending from an open proximal (20) end to an open distal (30) end, and a fluidic adapter (40) at the proximal (20) end in fluid connection the capillary tube lumen (12), wherein the capillary tube shaft (10) is adapted for dismountable insertion into a fluid-carrying lumen (212) of a bodily invasive tube (200), and the adapter (40) provides fluidic access to the capillary tube lumen (12) that is fluidically isolated from access to the invasive tube lumen (212). It further relates to an applicator package comprising the capillary tube assembly (100) and an applicator (510).

22 Claims, 23 Drawing Sheets

(51) Int. Cl.
    *A61M 5/178*     (2006.01)
    A61M 25/00     (2006.01)
    *A61B 5/03*     (2006.01)
    A61B 5/0215     (2006.01)
    A61M 25/01     (2006.01)

(52) U.S. Cl.
    CPC ....... *A61M 25/0026* (2013.01); *A61M 25/0021* (2013.01); *A61M 2025/0004* (2013.01); *A61B 5/031* (2013.01); *A61M 25/0097* (2013.01); *A61M 2025/0175* (2013.01); *A61B 5/0215* (2013.01); *A61M 25/0111* (2013.01); *Y10S 604/905* (2013.01)
    USPC ................ 604/171; 604/164.01; 604/905

(56) References Cited

U.S. PATENT DOCUMENTS

| | | | | |
|---|---|---|---|---|
| 3,335,723 | A * | 8/1967 | Waldman, Jr. | 604/163 |
| 3,595,230 | A * | 7/1971 | Suyeoka et al. | 604/192 |
| 3,709,223 | A * | 1/1973 | Macalalad et al. | 604/162 |
| 3,825,001 | A * | 7/1974 | Bennet et al. | 604/170.02 |
| 3,902,500 | A * | 9/1975 | Dryden | 128/207.14 |
| 4,099,528 | A * | 7/1978 | Sorenson et al. | 604/44 |
| 4,192,319 | A * | 3/1980 | Hargens et al. | 600/561 |
| 4,224,943 | A * | 9/1980 | Johnson et al. | 604/28 |
| 4,327,723 | A * | 5/1982 | Frankhouser | 604/171 |
| 4,327,735 | A * | 5/1982 | Hampson | 604/171 |
| 4,423,740 | A * | 1/1984 | Castle et al. | 600/561 |
| 4,613,329 | A * | 9/1986 | Bodicky | 604/158 |
| 5,149,326 | A * | 9/1992 | Woodgrift et al. | 604/163 |
| 5,156,596 | A * | 10/1992 | Balbierz et al. | 604/164.11 |
| 5,207,648 | A * | 5/1993 | Gross | 604/164.09 |
| 5,234,411 | A * | 8/1993 | Vaillancourt | 604/171 |
| 5,290,242 | A * | 3/1994 | Vaillancourt | 604/163 |
| 5,354,267 | A * | 10/1994 | Niermann et al. | 604/32 |
| 5,484,416 | A * | 1/1996 | Gittings | 604/164.08 |
| 5,573,007 | A | 11/1996 | Bobo, Sr. | |
| 5,582,599 | A * | 12/1996 | Daneshvar | 604/263 |
| 5,700,251 | A * | 12/1997 | Miyauchi et al. | 604/264 |
| 5,730,123 | A * | 3/1998 | Lorenzen et al. | 128/207.14 |
| 5,733,267 | A * | 3/1998 | Del Toro | 623/1.11 |
| 6,146,373 | A * | 11/2000 | Cragg et al. | 604/523 |
| 6,391,010 | B1 | 5/2002 | Wilcox | |
| 6,730,063 | B2 * | 5/2004 | Delaney et al. | 604/173 |
| 7,887,529 | B2 * | 2/2011 | Eder | 604/523 |
| 8,066,678 | B2 * | 11/2011 | Vaillancourt et al. | 604/198 |
| 8,529,549 | B2 * | 9/2013 | Tanghoj et al. | 604/544 |
| 2003/0032937 | A1 * | 2/2003 | Griego et al. | 604/508 |
| 2003/0216685 | A1 | 11/2003 | Porter | |
| 2004/0024294 | A1 | 2/2004 | Wellnhofer | |
| 2005/0267417 | A1 | 12/2005 | Secrest et al. | |
| 2009/0182201 | A1 | 7/2009 | Kucklick et al. | |

FOREIGN PATENT DOCUMENTS

| | | |
|---|---|---|
| DE | 9302891 U1 | 4/1993 |
| DE | 20112949 U1 | 11/2001 |
| DE | 202008010700 U1 | 10/2008 |
| EP | 1514512 A1 | 3/2005 |
| FR | 2 386 312 | 11/1978 |
| WO | WO 2005/058404 | 6/2005 |
| WO | WO 2005/070110 | 8/2005 |
| WO | WO 2010/023460 A1 | 3/2010 |

OTHER PUBLICATIONS

International Search Report and Written Opinion dated Oct. 25, 2011 issued to international priority application No. PCT/EP2011/062810.

* cited by examiner

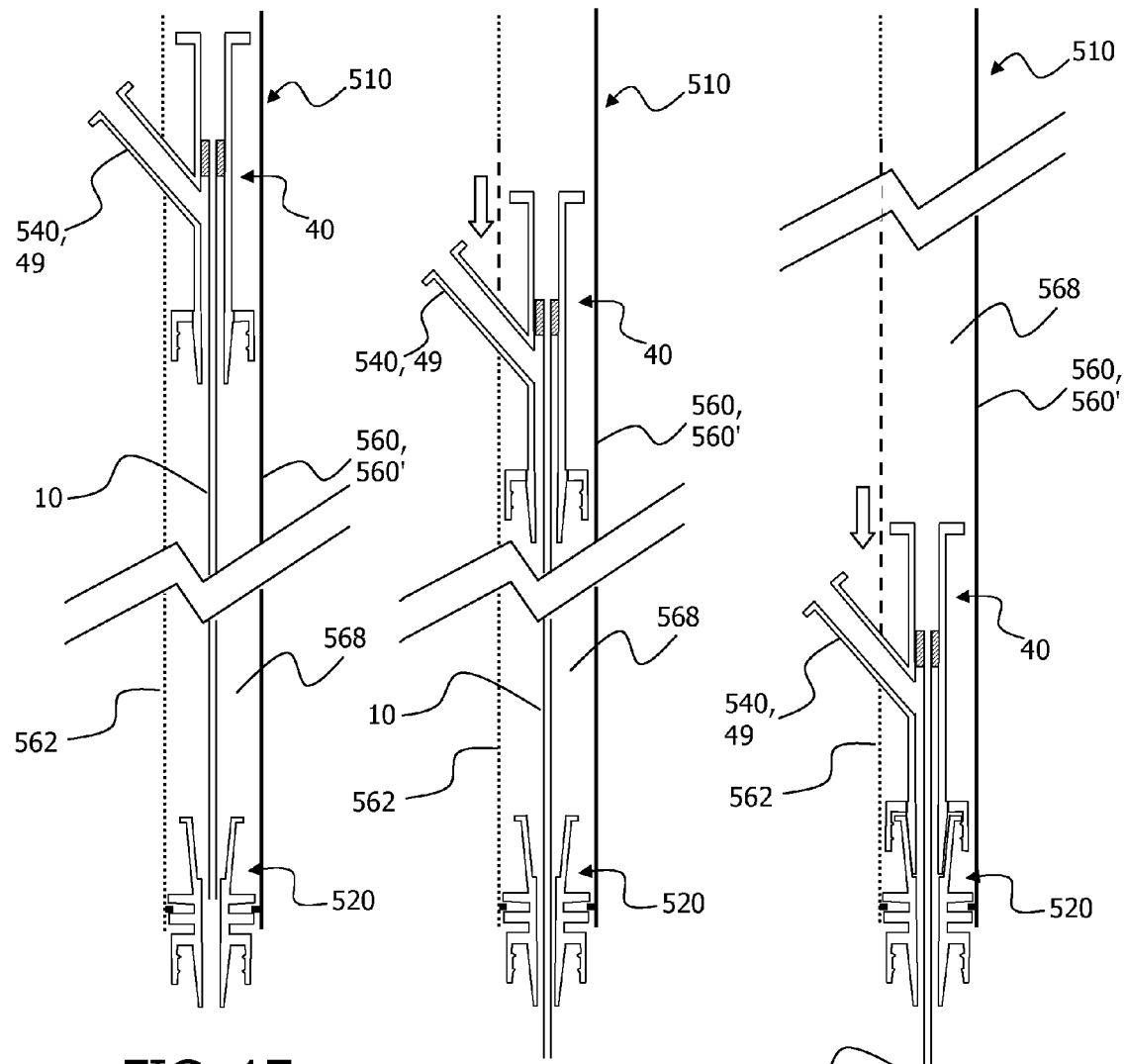

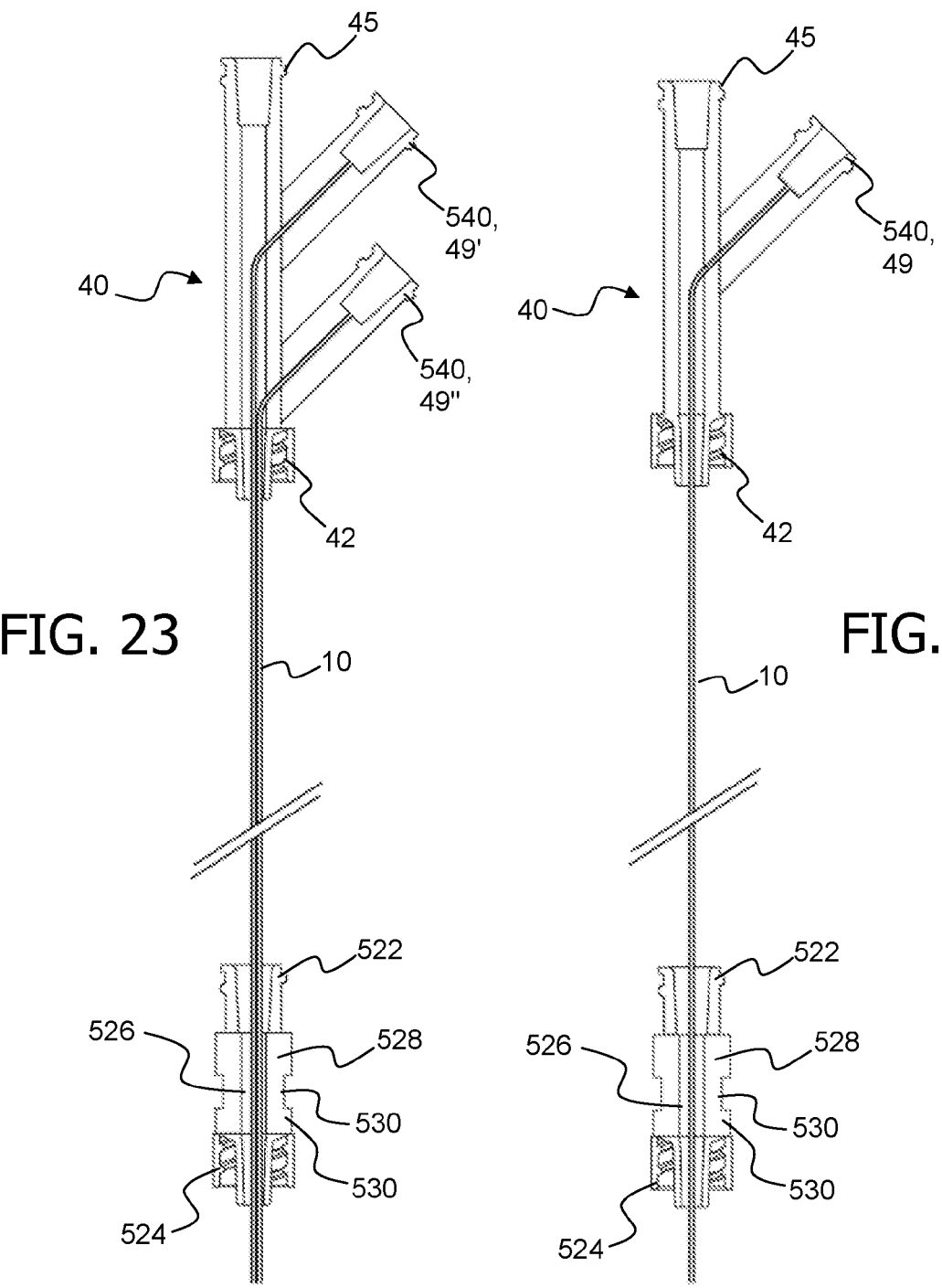

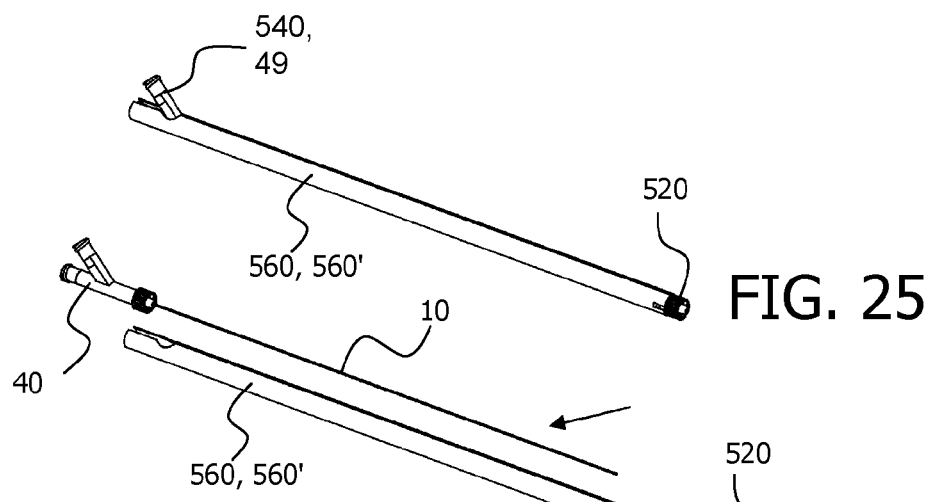
FIG. 25
FIG. 26
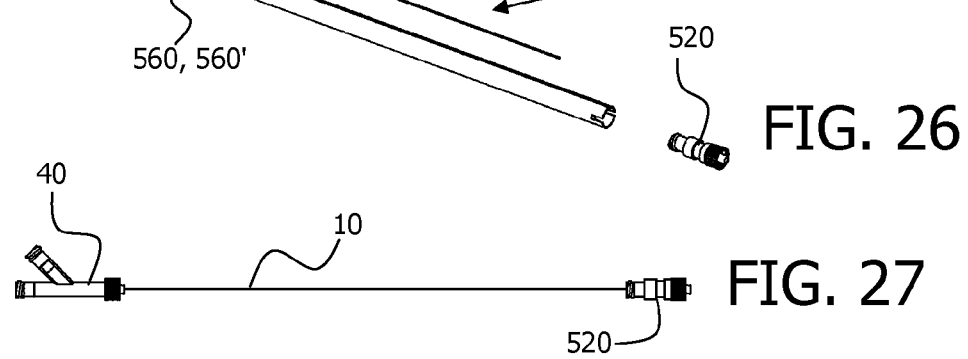
FIG. 27
FIG. 28
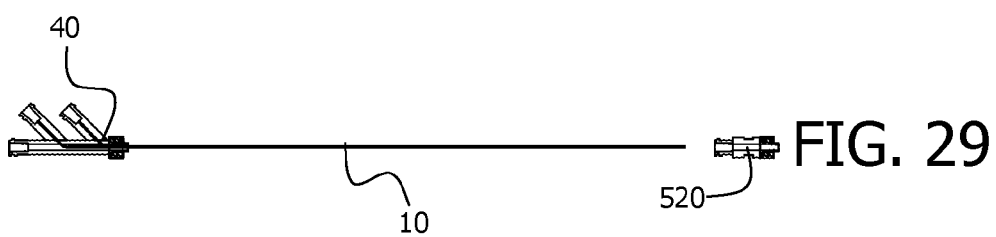
FIG. 29

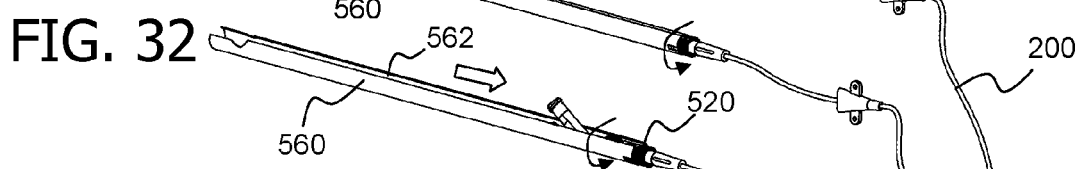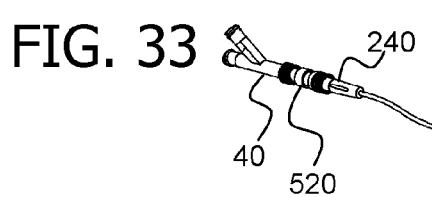

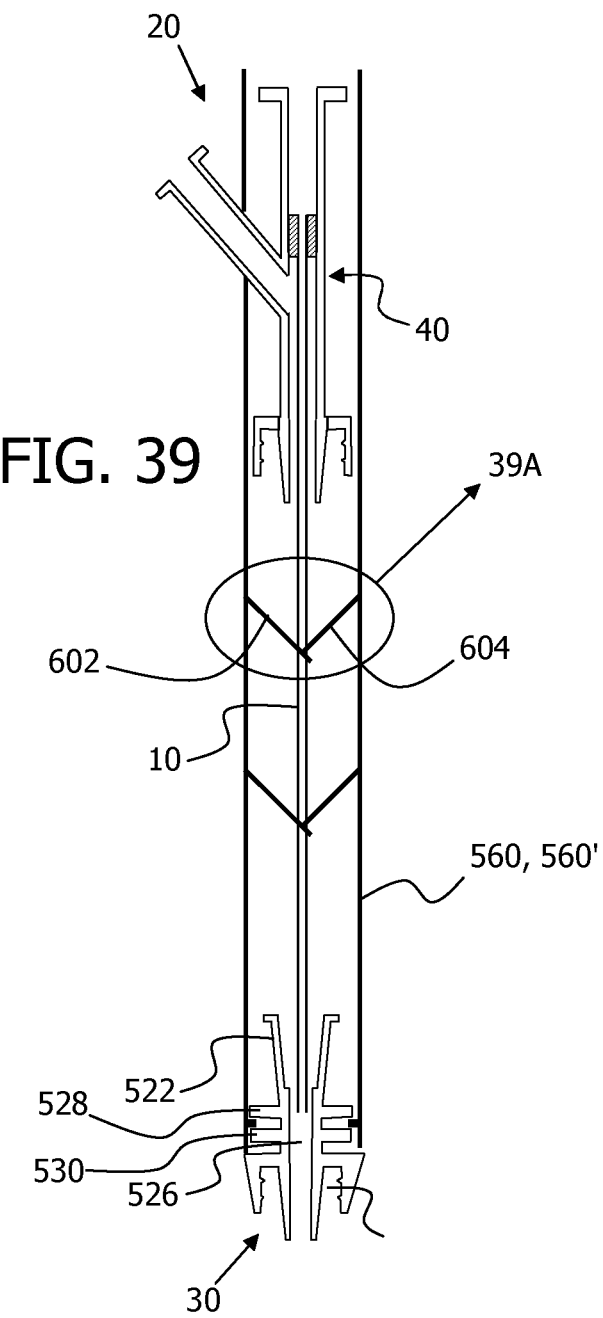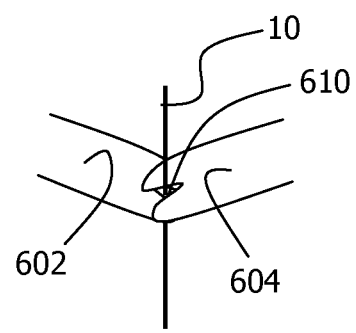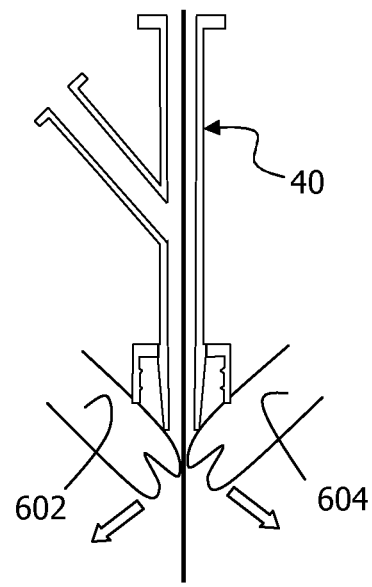

CAPILLARY TUBE ASSEMBLY

CROSS-REFERENCE TO RELATED APPLICATIONS

This application is the U.S. National Phase under 35 U.S.C. §371 of International Application PCT/EP2011/062810, filed Jul. 26, 2011, which claims priority to U.S. Provisional Application No. 61/367,795, filed Jul. 26, 2010; U.S. Provisional 61/434,676, filed Jan. 20, 2011; EP 10170794.1, filed Jul. 26, 2010; and EP 11151530.0, filed Jan. 20, 2011.

FIELD OF THE INVENTION

The present invention relates to the field of invasive medical tubing, more specifically to catheters and lumbar puncture needles.

BACKGROUND OF THE INVENTION

During hospitalisation or a surgical procedure, there may be a need to swap a single lumen catheter to a multi-lumen or vice versa. An anesthetist may need to swap a single lumen catheter for a multi-lumen catheter, for example, to provide an additional channel for drug administration or pressure measurement. Using present techniques, the existing catheter is typically removed over a guidewire, and the replacement catheter is fed over the same guidewire to the location of the previous catheter. The procedure entails some risk. Notably, it is traumatic and can give rise to complications such as pneumothorax, hematothorax, nerve damage, accidental puncture of arteries, and stroke. Moreover, the handling of a second catheter leads to an increased risk of infection.

Classical multichannel catheters are made from an extruded solid tube containing multiple channels. A classical two channel (dual lumen) catheter 242 of the art is shown in FIG. 1, inserted through the jugular vein 112 into the right atrium 114 of the heart of a subject 110. Owing to the extrusion process, the internal channel walls are relatively thick, and the catheter is stiffer compared with a single lumen device. Any catheter is preferably soft in order to be minimally traumatic in respect of endothelium damage due to insertion and cardiac pulsations; existing multichannel catheter will less fulfill this preference due to the thickness of internal walls.

Normal pressure hydrocephalus (NPH) is characterized by a triad of cognitive impairment, gait disturbance and nocturesis. The diagnosis is often difficult due to the symptoms being similar to other disorders such as dementia or Parkinson's disease. Many patients go completely unrecognized and are never treated. The condition is due to the fact the intracranial pressure (ICP) pressure is abnormal. It has been confirmed that pressure is increased due reduced absorption capacity. Therefore, a shunting device which drains the cerebro-spinal fluid (CSF) from the brain towards the abdomen or bloodstream is the principal therapy.

Several diagnostic procedures are currently used to make the diagnosis of NPH, which include magnetic resonance imaging (MRI), a lumbar puncture tap test, or measurement of absorption capacity. For the latter, saline is infused into the CSF space while the pressure is measured. A steep rise in pressure indicates reduced absorption. Infusion is normally performed through a lumbar puncture needle while the pressure is monitored through a second lumbar puncture needle. Some neurosurgeons use one large diameter needle for both infusion and monitoring. Infusion and monitoring through one fine needle is impossible since the dynamic resistance causes a false increased pressure reading. The issue with multiple or large lumbar puncture needles is the discomfort for the patient and the higher risk of post puncture hypotension headache. In the case of a large diameter needle, the small hole in the lumbar spinal dura caused by the puncture does not close spontaneously after measurement. In upright position the high hydrostatic pressure will cause an escape of CSF. The reduced pressure in the brain causes severe headaches.

There is thus a need for a device which can overcome the problems of the art.

SUMMARY OF SOME ASPECTS THE INVENTION

The invention relates to a detachable device for adding one or more channels to a bodily invasive tube (200), comprising a capillary tube assembly (100) described herein. The invasive tube (200) is preferably a central venous catheter The invention relates to a capillary tube assembly (100) having a proximal (20) end and a distal (30) end, comprising:
  a capillary tube shaft (10) disposed with a capillary lumen (12) extending from an open proximal (20) end to an open distal (30) end, and
  a fluidic adapter (40) at the proximal (20) end in fluid connection the capillary tube lumen (12),
wherein
  the capillary tube shaft (10) is adapted for dismountable insertion into a fluid-carrying lumen (212) of a bodily invasive tube (200), and
  the adapter (40) provides fluidic access to the capillary tube lumen (12) that is fluidically isolated from access to the invasive tube lumen (212).

The bodily invasive tube (200) is preferably a central venous catheter. The capillary tube shaft (10) is preferably thin walled.

The adapter (40) may be configured for dismountable connection to a coupling (240) on
the invasive tube (200), and
the invasive tube (200) may comprise:
  a hollow longitudinal shaft (210) having a proximal (20) end and a distal (30) end, disposed with an invasive tube lumen (212) extending from an open proximal (20) end to an open distal (30) end, and
  a coupling (240) at the proximal end (20) in fluid connection with the invasive tube lumen (212),
which hollow longitudinal shaft (210) is configured for introduction into a bodily lumen from its distal (30) end.

The capillary tube shaft (10) may be further configured to avoid occlusion of the invasive tube lumen (212) while the capillary tube shaft (10) is inserted.

The adapter (40) has distal (30) end and proximal (20) end, wherein:
  the distal (30) end may be provided with a fluidic connector (42) configured for dismountable fluidic connection to the coupling (240) of the invasive tube (200), and
  the proximal end may be provided with a fluidic connector (45) in fluid connection with the capillary tube lumen (12) for dismountable fluidic connection to a reciprocating fluidic connector, and
  the proximal and distal end fluidic connectors (42, 45) may be fluidically isolated in the adapter (40).

The adapter (40) may further provided with a side port in fluid connection with the distal end fluidic connector (42) of the adapter (40).

The capillary tube shaft may be formed at least partially, preferably entirely from polyimide.

The capillary tube may have:
an external diameter of 0.2 mm to 0.6 mm or 0.2 to 0.9 mm, and
a wall thickness of 0.02 mm to 0.13 mm.

The device or capillary tube assembly (100) may be packaged in an applicator (510) comprising:
a longitudinal protective cover (560) having a proximal end (20) and a distal end (30),
an opening at the distal end (30),
wherein
the protective cover forms a void (568) in which the capillary tube shaft (10) and at least a distal part of the adapter (40) are disposed,
the cover is configured such that the capillary tube shaft (10) is slidable relative to the opening at the distal end (30).

The opening at the distal end may be sealed with a detachable seal. An intermediate coupling (520) may be dismountably attached through the opening at the open distal end of the cover (560), which coupling has a proximal (20) and distal (30) end, a fluidic coupling (522) at the proximal (20) end of the intermediate coupling (520) configured for attachment to the adapter (40) of the capillary tube assembly (100) and a fluidic coupling (524) at the distal (30) end of the intermediate coupling (520) configured for attachment to a coupling (240) on the invasive tube (200), both fluidic couplings (522, 524) of the intermediate coupling (520) joined to an internal chamber (526),
wherein
at least a proximal part of the intermediate coupling (520) is deposed in the void (568) of the protective cover (560), and
the distal end of the capillary tube shaft (10) is positioned in the fluidic coupling (522) at the proximal (20) end of the intermediate coupling (520)

The protective cover (560) may be comprised in a rigid, hollow protective tube (560') having a proximal (20) and distal end (30), and a breachable seal (562) disposed along the longitudinal length of the wall of the tube (560'), and the breachable seal (562) may be configured to breach as the adapter (40) is slidably advanced towards the intermediate coupling (520).

The capillary tube assembly may be packaged in an applicator package comprising:
a rigid, hollow protective tube (560) having a proximal (20) and distal end (30), and a breachable seal (562) disposed along the longitudinal length of the wall of the tube (560),
an intermediate coupling (520) having a fluidic coupling (522) at its proximal (20) end configured for attachment to the adapter (40) of the capillary tube assembly (100) and a fluidic coupling (524) at its distal (30) end configured for attachment to the coupling (240) of the invasive tube (200), both fluidic couplings (522, 524) joined to an internal chamber (526),
wherein
the intermediate coupling (520) is dismountably attached to the distal end (30) of the protective tube,
the capillary tube assembly (100):
is dismountably attached to the proximal end (30) of the protective tube (560),
is slidably mounted in the hollow protective tube (560), and
is configured to slide relative to the intermediate coupling (520),
the capillary tube shaft (10) is positioned within the couplings (522, 524) and/or chamber (526) of the intermediate coupling (520), and
the breachable seal (562) is configured to breach as the capillary tube assembly (100) is slidably advanced towards the intermediate coupling (520).

The capillary tube assembly (100) may be dismountably attached to the protective tube (560) using a handle (540) attached to the adapter (40) that protrudes through the breachable seal (562) of the protective tube (560), The handle (540) attached to the adapter (40) may be:
a side port attached to the adapter (40) in fluid connection with the distal end fluidic connector (42) of the adapter (40), or
a handle member (542) dismountably attached to the adapter (40).

The protective cover (560) may be comprised in a longitudinal flexible pouch (560") having a proximal (20) and distal end (30).

The adapter (40) may be dismountably attached to the proximal end of the flexible pouch (560").

The protective cover (560) may be comprised in a longitudinal hollow bellows tube (560'") having a proximal (20) and distal end (30), and comprising at least a bellowed portion of tubing.

The adapter (40) may be dismountably attached to the proximal end of the pouch.

The adapter (40) may be dismountably attached to the bellows tube (560'") using a handle (540) attached to the adapter (40) that protrudes through a side opening (570) of the bellows tube (560'").

The handle (540) may be:
a side port attached to the adapter (40) in fluid connection with the distal end fluidic connector (42) of the adapter (40), or
a handle member dismountably attached to the adapter (40).

The invasive tube (200) may be a catheter (200') comprising a hollow longitudinal shaft (210') having an open proximal (20) end and an open distal (30) end, and a coupling (240') at the proximal end (20) in fluid connection with the catheter lumen (212'), which hollow longitudinal shaft (210') is configured for introduction into the bodily lumen from its distal (30) end.

The invasive tube (200) may be a lumber puncture needle (200") comprising a hollow longitudinal shaft (210") having an open proximal (20) end and an open distal (30) end, a sharpened distal (30) end, and a coupling (240') at the proximal end (20) in fluid connection with the catheter lumen (212'), which hollow longitudinal shaft (210') is configured for introduction into the bodily lumen from its distal (30) end.

The capillary tube shaft (10) may be disposed with more than one capillary lumens (12) extending from an open proximal (20) end to an open distal (30) end, and a separate fluidic adapter (40) at the proximal (20) end is in fluid connection with each capillary tube lumen (12).

The hollow longitudinal shaft (210) may comprise more than one invasive tube lumens (212) extending from an open proximal (20) end to an open distal (30) end, and a separate fluidic adapter (240) at the proximal (20) end is in fluid connection with each invasive tube lumen (212).

The central venous catheter may comprise a hollow longitudinal shaft (210) having an open proximal (20) end and an open distal (30) end, said hollow longitudinal shaft (210) may comprise one or more central venous catheter lumens (212) extending from an open proximal (20) end to an open distal

(30) end, and a separate fluidic coupling (240) at the proximal (20) end is in fluid connection with each invasive tube lumen (212).

The invention further relates to a kit comprising a capillary tube assembly (100) as described above and further comprising the invasive tube (200) as described above.

The invention further relates to a method for adapting an existing catheter (200') to provide an additional lumen, said catheter provided with at least one catheter lumen (212') extending between an open distal (30) end and an open proximal (20) end for conductance of a fluid, and a coupling (240') at the proximal (20) end in fluid connection with said catheter lumen (212'), comprising the steps:
- inserting the distal (30) end of a capillary tube assembly (100) or device as described herein into the lumen (212') of the catheter through its open proximal (20) end,
- connecting the adapter (40) of the capillary tube assembly (100) to the coupling (240') of the catheter (200'),
- thereby providing the catheter (200') with an additional lumen which is the capillary tube lumen (12).

FIGURE LEGENDS

FIGS. 17 to 19 depict a cross-sectional view in a plane parallel to the longitudinal direction of an applicator package of the invention that comprises a protective rigid tube; it shows the stages of advancing the capillary tube assembly within an applicator of the invention, wherein handle is formed from a side port of the catheter tube assembly adapter.

FIG. 23 depict a cross-sectional view in a plane parallel to the longitudinal direction of a capillary tube assembly mounted on an intermediate coupling, in which the adapter is provided with two side ports each in fluid connection with a separate lumen of a dual lumen capillary tube.

FIG. 24 depicts a cross-sectional view in a plane parallel to the longitudinal direction of a capillary tube assembly mounted on an intermediate coupling, in which the adapter has a single side port in fluid connection with the lumen of a single lumen capillary tube.

FIG. 25 depicts a perspective view of an applicator package of the invention comprising a protective rigid tube in an assembled state.

FIG. 26 depicts a perspective view of an applicator package of the invention comprising a protective rigid tube in a disassembled state.

FIG. 27 depicts a perspective view of an applicator package of the invention comprising a protective rigid tube in an assembled state, wherein the protective tube has been removed to reveal the arrangement of capillary tube assembly and intermediate coupling.

FIG. 28 depicts a cross-sectional view in a plane parallel to the longitudinal direction of a capillary tube assembly and intermediate coupling of an applicator package; the capillary tube assembly is single lumen, served by a Y-shaped adapter.

FIG. 29 depicts a cross-sectional view in a plane parallel to the longitudinal direction of a capillary tube assembly and intermediate coupling of an applicator package; the capillary tube assembly is double lumen, served by a double Y-shaped adapter.

FIGS. 30 to 33 show the stages of deploying the catheter tube assembly into the lumen of a catheter using an applicator of the invention comprising a protective rigid tube.

Figure 34:
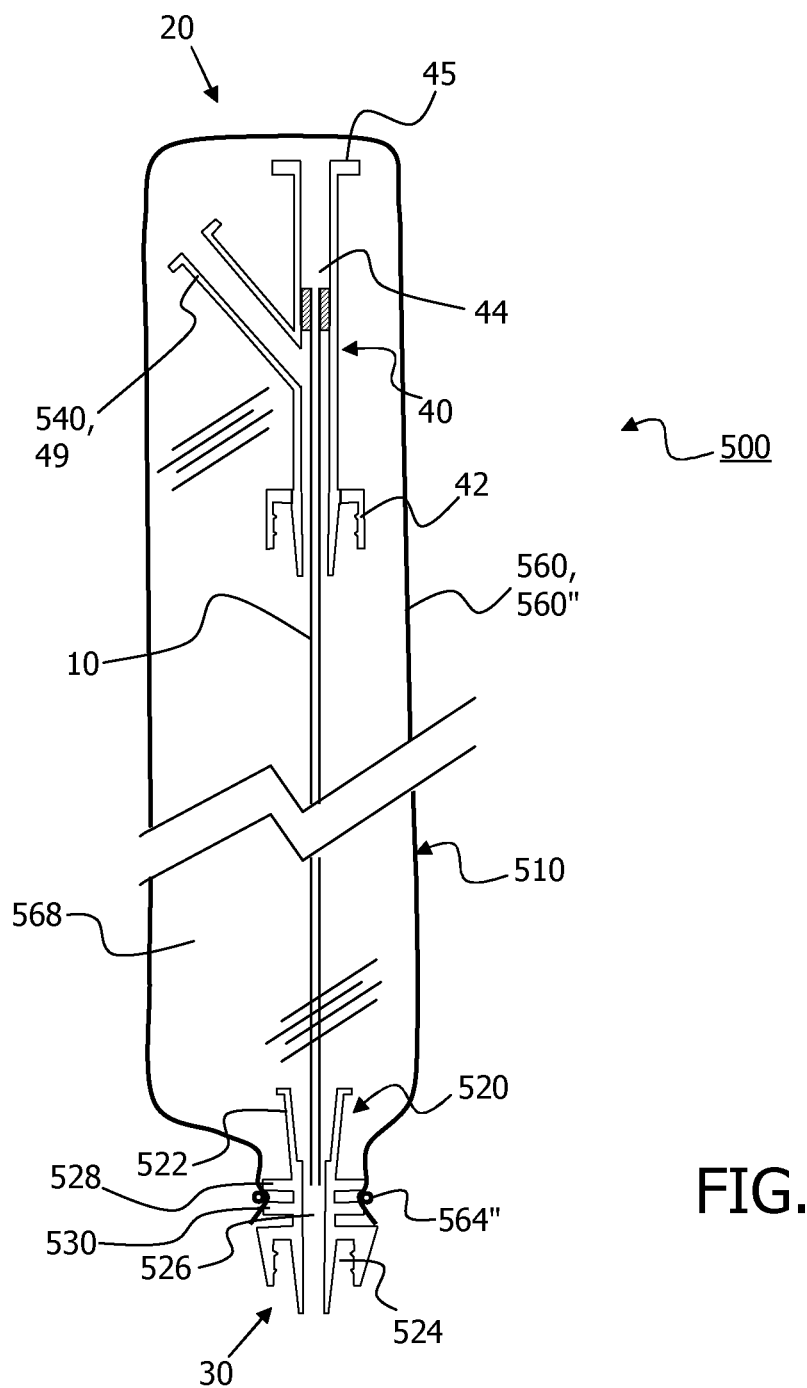

FIG. 34 shows an applicator of the invention in which the protective cover is a flexible pouch which encloses the adapter. An intermediate coupling is mounted at the distal end. A catheter tube assembly is disposed in the applicator.

Figure 35:
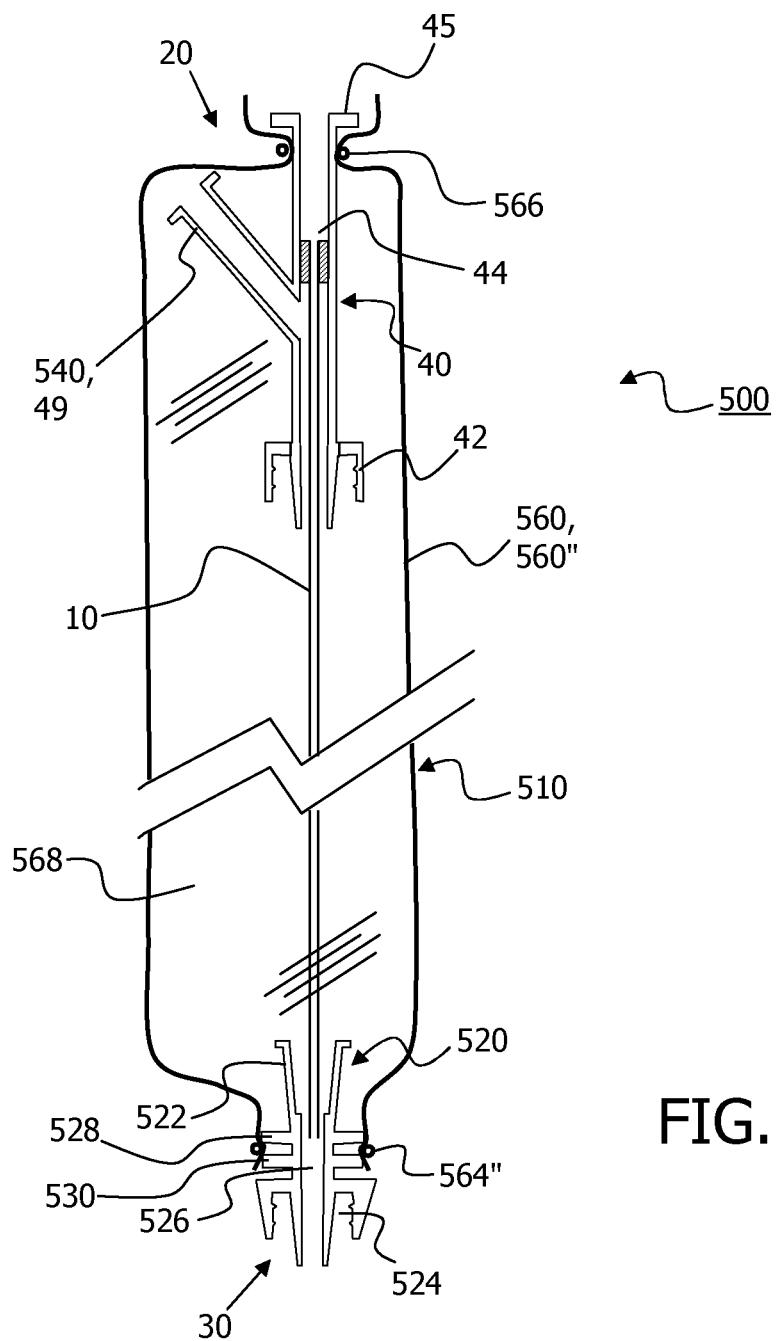

FIG. 35 shows an applicator of the invention in which the protective cover is a flexible pouch that is attached at the proximal end to the adapter, and whereby the adaptor protrudes from the proximal end of the pouch. An intermediate coupling is mounted at the distal end. A catheter tube assembly is disposed in the applicator.

Figure 36:
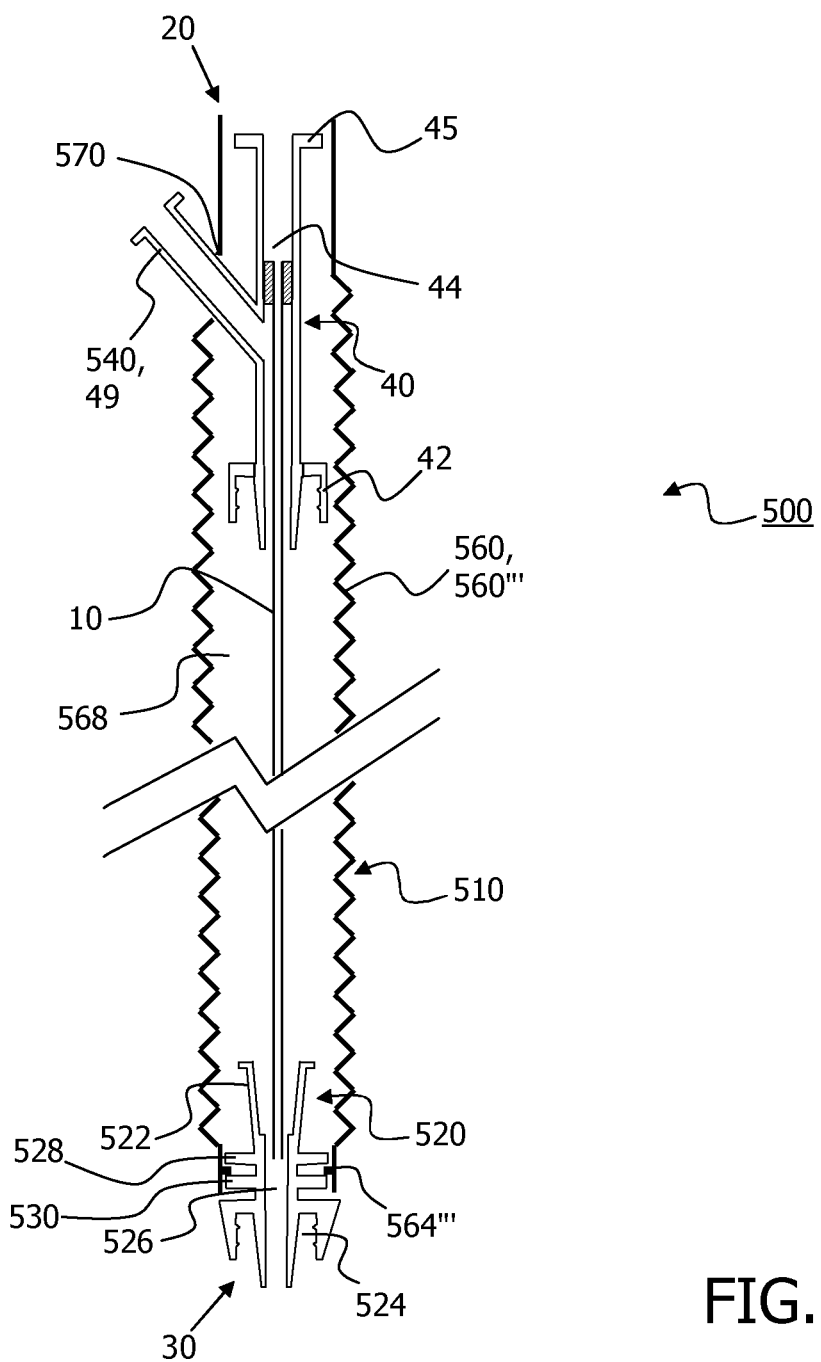

FIG. 36 shows an applicator of the invention in which the protective cover is a flexible pouch that is collapsible bellows tube. A catheter tube assembly is disposed in the applicator.

Figure 37:
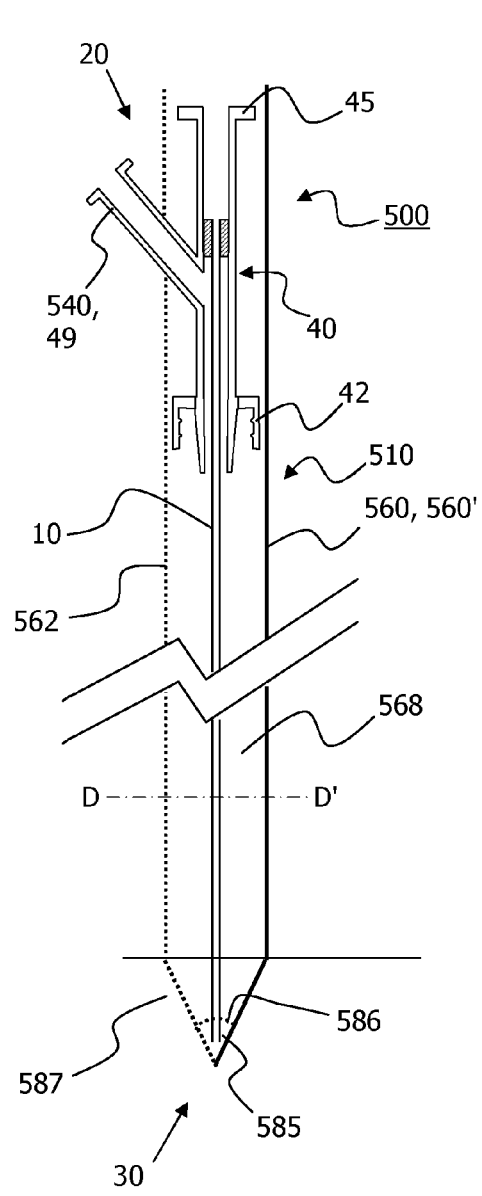

FIG. 37 depicts a cross-sectional view in a plane parallel to the longitudinal direction of an applicator of the invention that comprises a protective rigid tube, in which the adapter is provided with a side port. A catheter tube assembly is disposed in the applicator. The intermediate coupling is absent; the distal end of the protective rigid tube is pointed.

Figure 38:
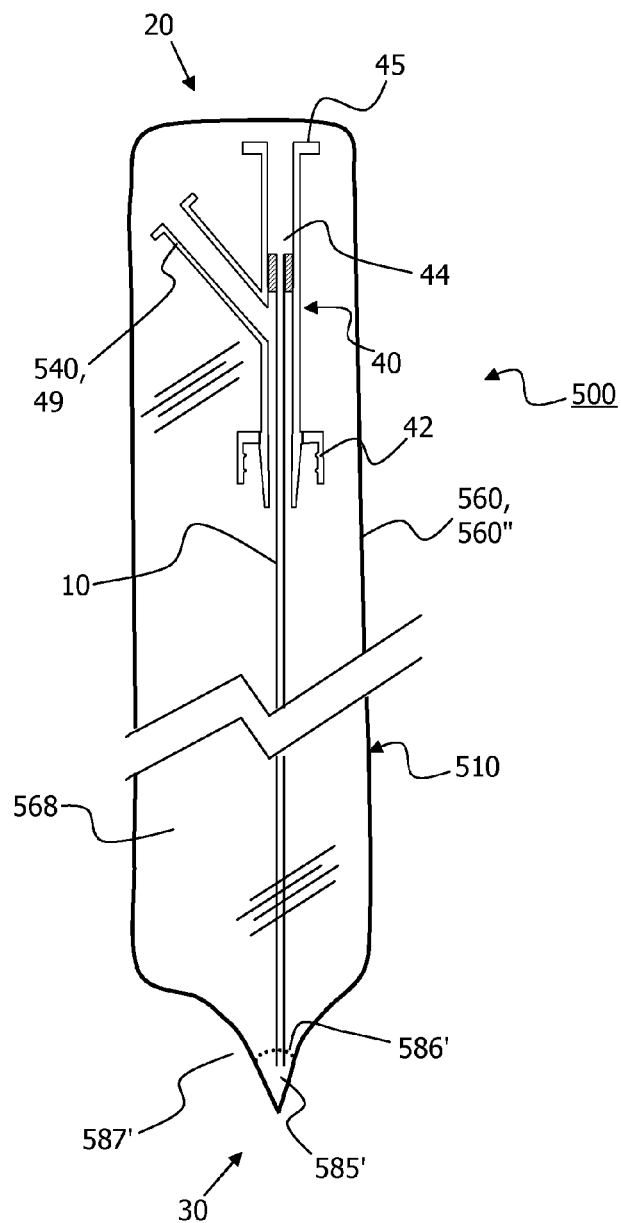

FIG. 38 shows an applicator of the invention in which the protective cover is a flexible pouch which encloses the adapter. The intermediate coupling is absent; the distal end of the flexible pouch is pointed. A catheter tube assembly is disposed in the applicator.

FIG. 39 depicts a cross-sectional view in a plane parallel to the longitudinal direction of an applicator of the invention that comprises a protective rigid tube. A catheter tube assembly is disposed in the applicator. The inside wall of the protective rigid tube is disposed with diametrically opposed pairs of inclined barbs.

FIG. 39A depicts a detailed view of FIG. 39 (39A) of a pair of diametrically opposed inclined barbs which form an orifice for holding the capillary tube shaft.

Figure 41:
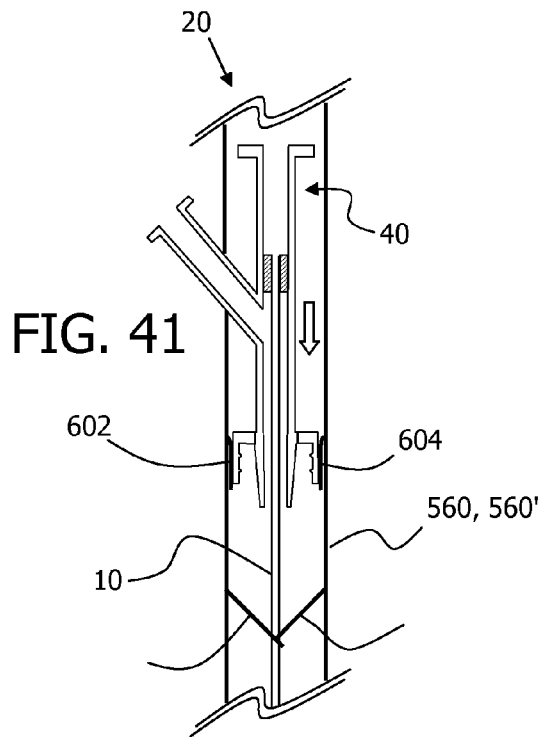

FIGS. 40 to 41 depicts the effect of the adapter in forcing the inclined barbs aside.

Figure 42:
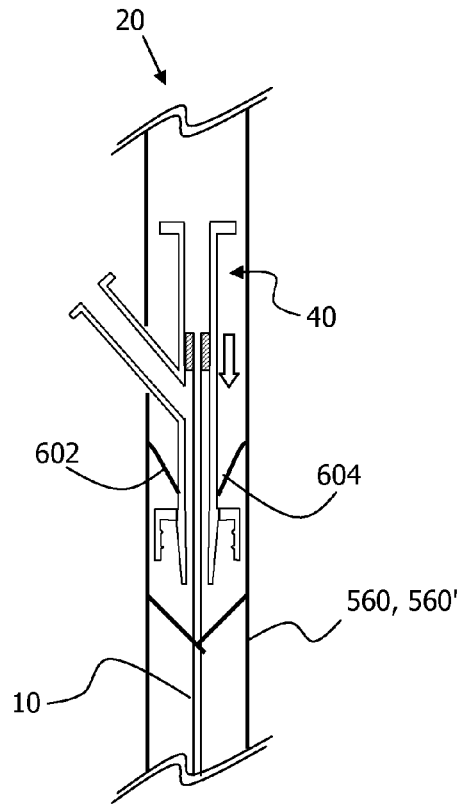

FIG. 42 depicts when the distal end of the adapter has passed a barb.

Figure 43:
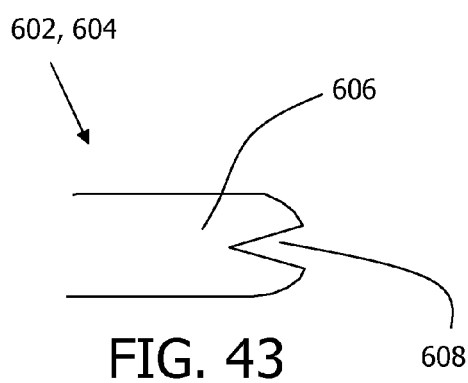

FIG. 43 depicts a plan view of a barb.

DETAILED DESCRIPTION OF THE INVENTION

Before the present system and method of the invention are described, it is to be understood that this invention is not limited to particular systems and methods or combinations described, since such systems and methods and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any or etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects and embodiments of the invention are defined in more detail. Each aspect and embodiment so defined may be combined with any other aspect(s) and embodiment(s) unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

The terms "distal", "distal end", "proximal" and "proximal end" are used through the specification, and are terms generally understood in the field to mean towards (proximal) or away (distal) from the surgeon side of the apparatus. Thus, "proximal (end)" means towards the surgeon side and, therefore, away from the patient side. Conversely, "distal (end)" means towards the patient side and, therefore, away from the surgeon side. Herein, the "proximal (end)" of an element is denoted with reference sign 20, and the "distal (end)" of an element is denoted with reference sign 30.

In the following detailed description of the invention, reference is made to the accompanying drawings that form a part hereof, and in which are shown by way of illustration only of specific embodiments in which the invention may be practiced. It is to be understood that other embodiments may be utilised and structural or logical changes may be made without departing from the scope of the present invention. The following detailed description, therefore, is not to be taken in a limiting sense, and the scope of the present invention is defined by the appended claims.

Figure 1:
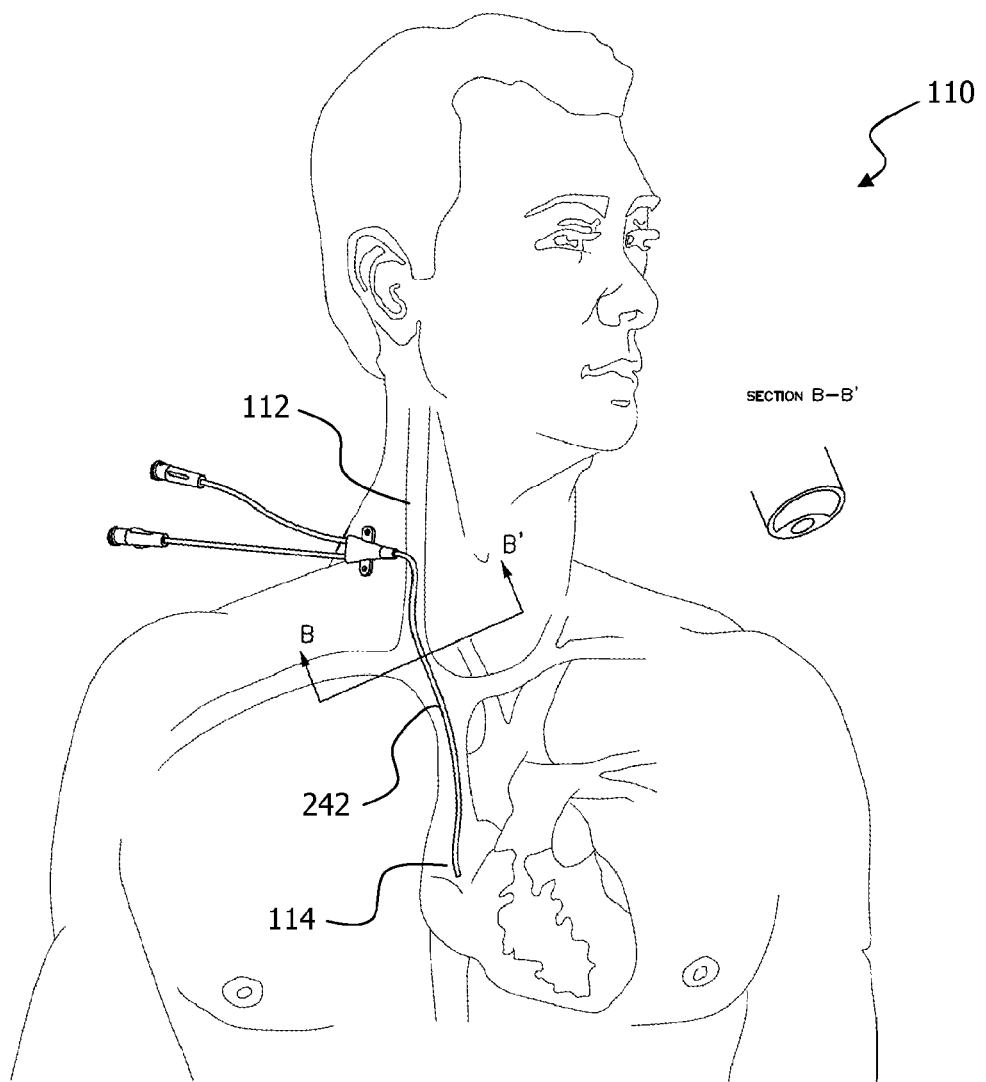
FIG. 1 depicts a dual lumen catheter of the art in-situ in a subject; inset is a view of a transverse section across the catheter at line B-B'.
Figure 2:
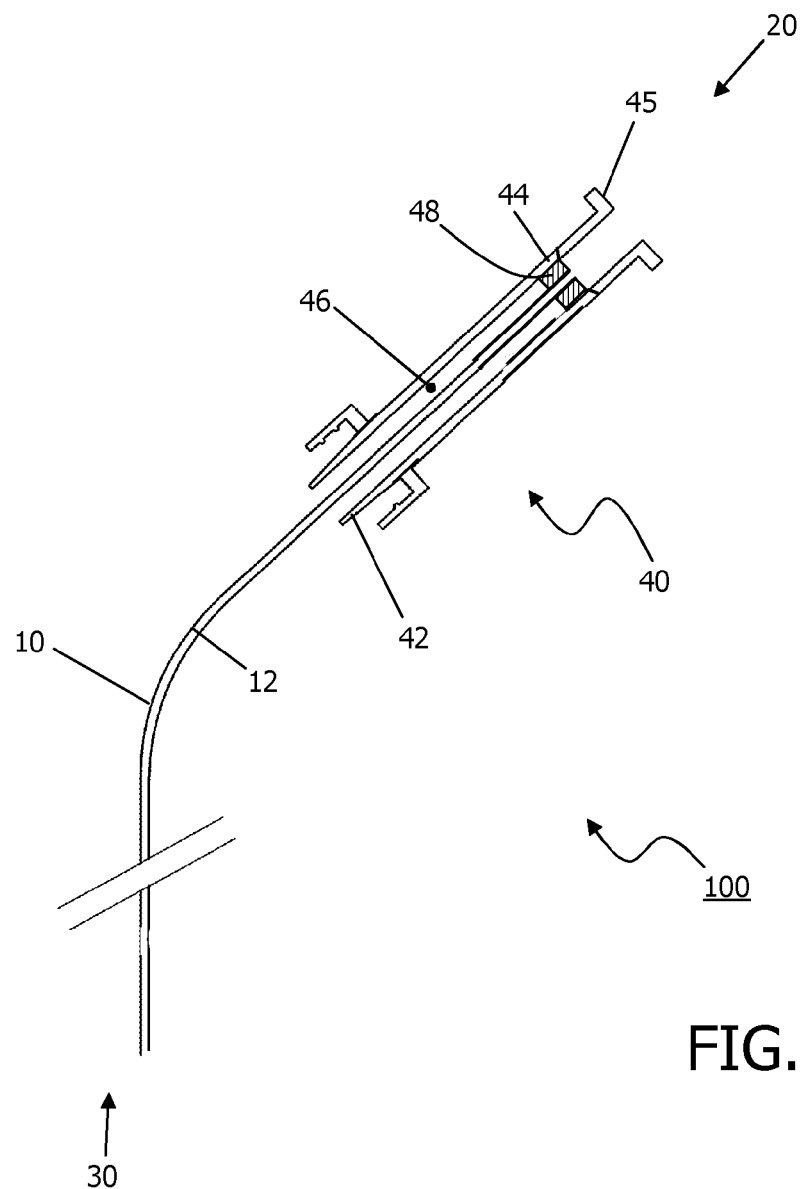
FIG. 2 depicts a cross-sectional view in a plane parallel to the longitudinal direction of a catheter tube assembly provided with an inline, Luer type adapter.
Figure 3:
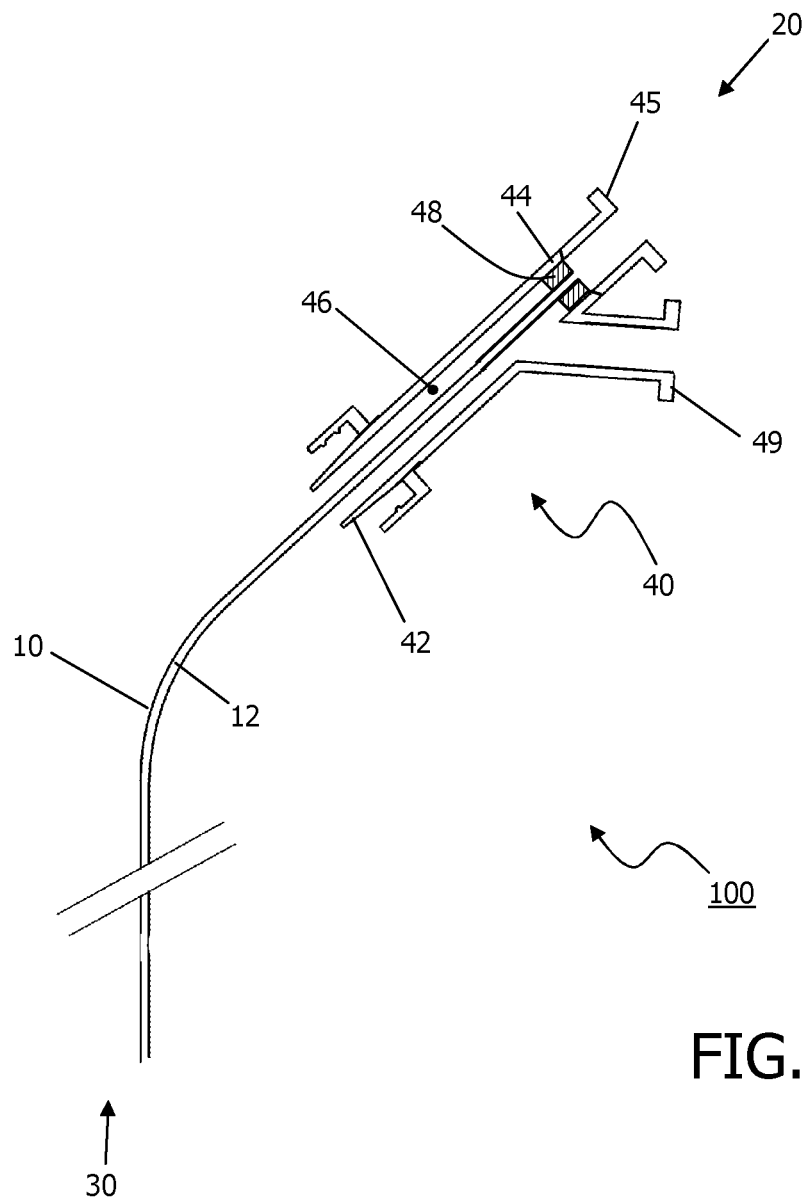
FIG. 3 depicts a cross-sectional view in a plane parallel to the longitudinal direction of a catheter tube assembly provided with a Y-shaped, Luer type adapter.

The present invention, as exemplified in FIGS. 2 and 3, concerns a dismountable or detachable device for adding one or more channels to a bodily invasive tube (200) that is preferably to a central venous catheter. The device comprises a capillary tube (10), an adapter (40) configured to fluidically isolate the capillary tube lumen (12) from a bodily invasive tube (200) lumen (212) and to maintain the functioning of the bodily invasive tube (200).

More specifically, the device comprises a capillary tube assembly 100 having a proximal 20 and distal end 30, which assembly 100 comprises a capillary tube shaft 10 disposed with at least one capillary lumen extending from the proximal 20 end to the distal 30 end and an adapter 40 at the proximal 20 end configured to provide fluidic access to the capillary tube lumen 12. The adapter is also configured for dismountable attachment to a coupling on an invasive tube (see later below). The adapter is also configured to isolate the capillary tube lumen 12 from the invasive tube lumen. When there are more than one capillary tube lumens, the capillary tube lumens are preferably fluidically isolated from each other within the shaft 10. Each lumen is preferably provided with a separate adapter 40. The capillary tube assembly 100 is adapted for dismountable insertion into a fluid-carrying lumen (invasive tube lumen) of a bodily invasive tube. More in particular, the distal 30 end of a capillary tube assembly 100 may be inserted into the lumen 212 of the invasive tube 200 through its open proximal 20 end.

Figure 5:
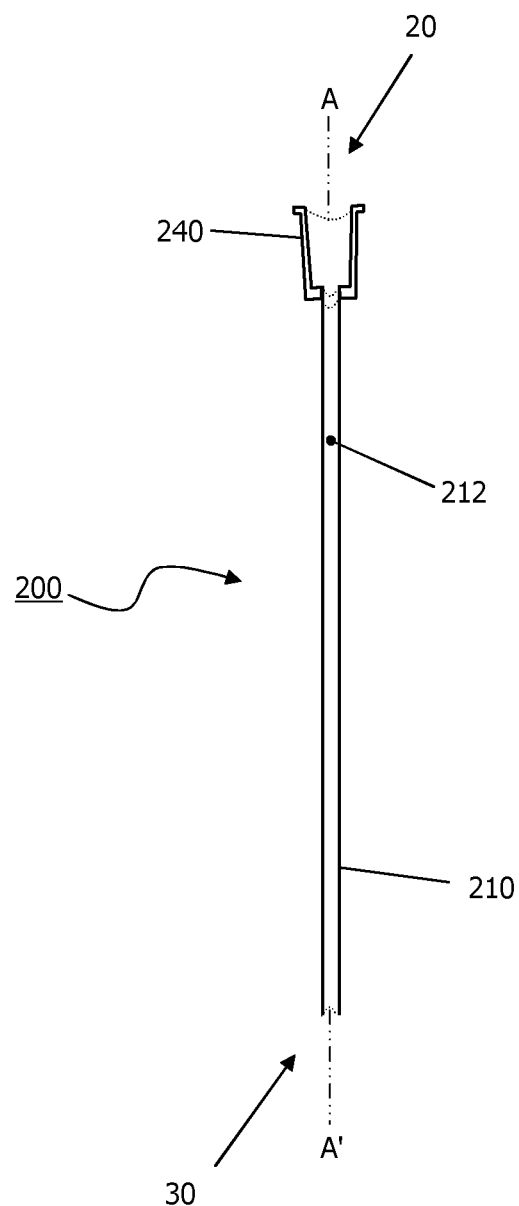
FIG. 5 depicts a cross-sectional view in a plane parallel to the longitudinal direction of a bodily invasive tube.

An invasive tube 200, exemplified in FIG. 5, has a distal end 30 and proximal end 20, and comprises a hollow invasive tube shaft 210 for insertion into a bodily vessel or cavity, disposed with at least one lumen 212 (invasive tube lumen) extending from an open proximal end 20 to an open distal end 30 and a coupling at the proximal 20 end configured to provide fluidic access to the invasive tube lumen 12 and for dismountable attachment to the adapter 40 of the capillary tube assembly 100. When there are more than one invasive tube lumens, the invasive tube lumens are preferably fluidically isolated from each other within the invasive tube shaft 210. Each lumen is preferably provided with a separate coupling 240. The invasive tube lumen 212 is adapted for receiving the capillary tube shaft 10 of the capillary tube assembly 100. When capillary tube assembly and invasive tube 200 are assembled, the invasive tube shaft 210 surrounds the capillary tube shaft 10, and the adapter provides independent fluidic access to the invasive tube lumen and capillary tube lumen 10.

The invasive tube lumen 212 from the proximal end can be fluidically accessed independent of the capillary tube lumen 12. The capillary tube shaft 10 is further configured such that passage of fluid through the invasive tube lumen 212 is maintained while the capillary tube 10 is inserted therein. In other words, the inserted capillary tube shaft 10 does not significantly obstruct the passage of fluid through the invasive tube lumen.

The fluid carried by the lumen described herein may be any, preferably it is a non-compressible fluid i.e. a liquid.

Figure 4:
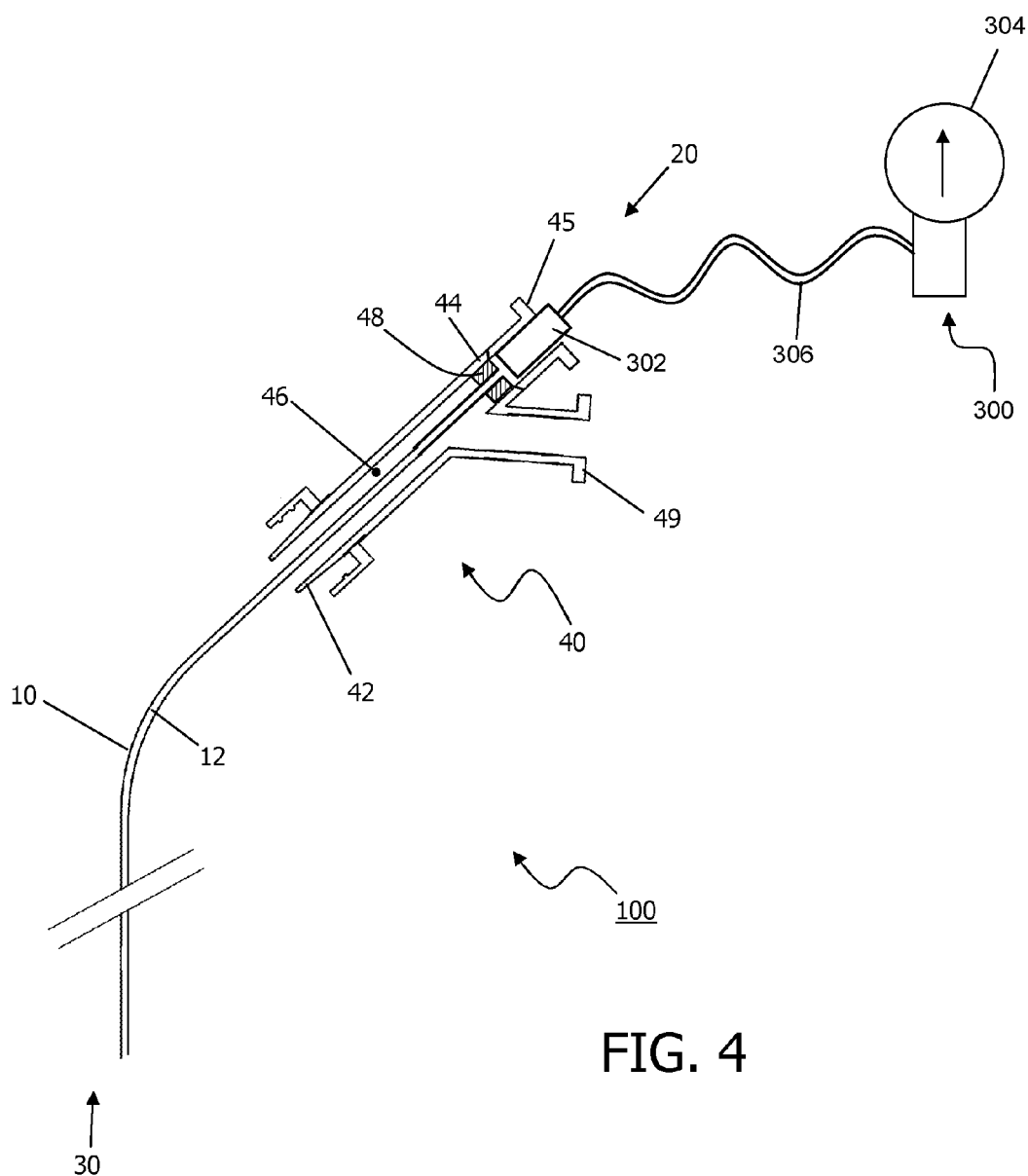
FIG. 4 depicts a cross-sectional view in a plane parallel to the longitudinal direction of a catheter tube assembly provided with a Y-shaped, Luer type adapter, attached via one port to a pressure gauge.

The capillary tube assembly 100 may be employed as a hydrostatic pressure detector, for measuring the pressure at the distal 30 tip of the invasive tube 200. The capillary tube lumen 12 may be filled with a non-compressible fluid for example, a liquid such as aqueous saline solution. Hydrostatic pressure in the vicinity of the distal open end of the capillary tube 10 is conducted along the lumen 12 by the non-compressible fluid to the open proximal 20 end of the capillary tube 10 where a pressure gauge 300 (FIG. 4) in dismountable fluidic connection with the lumen 12 measures the pressure transmitted from the distal end of the capillary tube 10. Absolute (or gauge) pressure in the vicinity of the distal open end of the capillary tube 10 can thus be recorded. FIG. 4 depicts a pressure gauge 300 provided with pressure tubing joined to a connector 302 for attachment to the adapter 40 of the capillary tube assembly 100.

More in particular, the adapter 40 is configured to allow the fluidic connection of the pressure gauge 304 to the open proximal 20 end of the capillary tube 10 while excluding the fluidic connection of said gauge 304 to the open proximal end 20 of the invasive tube 200. Hydrostatic pressure is thereby measured at the proximal 20 end of the capillary tube 10 to the exclusion of a hydrodynamic and hydrostatic measurement at the proximal 20 end of the invasive tube lumen 212.

Advantageously, the capillary tube assembly 100 provides a measurement of ambient pressure at the distal end of the invasive tube 200 that accurately reflects the static pressure in the cavity (e.g. blood vessel, lumbar cavity, bladder etc) into which the distal end of the invasive tube shaft 210 is inserted.

The pressure measurement capability of the capillary tube assembly 100 has application, for example, when the invasive tube 200 is a multilumen catheter. In particular said catheter has a rinse inlet channel, for the introduction of rinse medium into the cavity and having a separate drainage outlet channel for the drainage of medium from the cavity. The catheter thus operates in a continuous flow irrigation mode. Raised intracavity pressure during certain procedures for instance, raised intracranial pressure (ICP) during neurosurgical procedures, can induce intracranial hypertension leading to cardiovascular complications, herniation syndrome, retinal bleeding, Tersons's syndrome and excessive fluid resorption.

Cavity pressure that is measured conventionally i.e. using a pressure gauge attached to the proximal end of a rinse inlet of a multilumen invasive catheter would indicate a considerably higher pressure (e.g. 136 mmHg), while a pressure gauge attached to the proximal end of a rinse outlet of the multilumen invasive tube would indicate a much lower pressure (e.g. 42 mmHg). Measurement at the rinsing inlet gives a severe overestimation of the true cavity pressure, and if clinicians were to respond to these pressures, this would unnecessarily impede the rinsing efforts of the surgeon. Measurement at the outflow point gives a systematic severe underestimation of the true cavity pressure, which would delay crucial intervention. By employing the capillary tube assembly 100 inserted into the rinse inlet channel of the multilumen catheter, fresh rinse medium continually washes over the open distal end, removing or preventing blockages or contamination with particles.

The pressure measurement capability of the capillary tube assembly 100 has application, for example, when the invasive tube 200 is a central venous catheter (single channel or multi lumen). In many medical or surgical circumstances, close hemodynamic monitoring of the central venous pressure is essential. The central venous pressure (CVP) is the pressure of the blood in the caval veins, close to the heart. It is imperative to have a precise measurement of this pressure as it is essential for hemodynamic management of the most vulnerable patients. In clinical practice, the CVP is measured through a central venous catheter, where a channel is reserved only for measurement of this pressure. Sometimes, it is necessary to use this same channel for drug administration, however, this would inevitably cause an erroneous CVP-measurement because of the dynamical resistance (described by de Hagen-Poiseuille equation) of the lower part of the catheter system. The capillary tube assembly 100 allows one channel of the catheter to have separate pressure measurement and drug delivery functions, without sacrificing accuracy of the CVP measurement.

Figure 9:
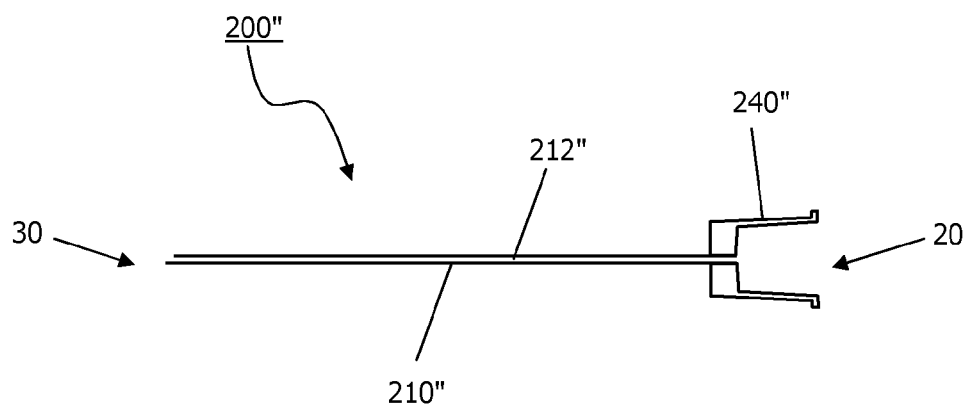
FIG. 9 depicts a cross-sectional view in a plane parallel to the longitudinal direction of a bodily invasive tube that is a lumber puncture needle.
Figure 11:
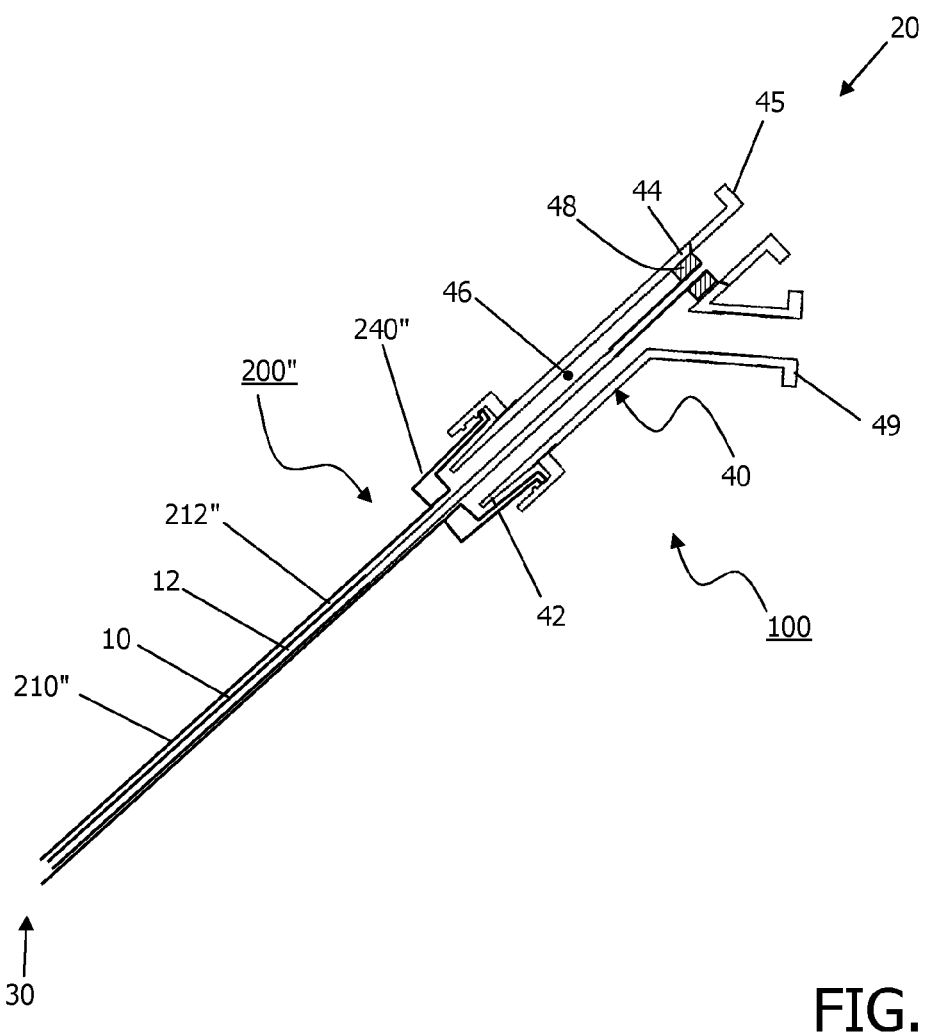
FIG. 11 depicts a cross-sectional view in a plane parallel to the longitudinal direction of a catheter tube assembly inserted into and connected with a bodily invasive tube that is a lumber puncture needle.

The pressure measurement capability of the capillary tube assembly 100 also has application when the invasive tube 200 is a lumbar puncture needle. An exemplary lumbar puncture needle 200" is shown in FIG. 9, FIG. 11 depicts said needle 200" onto which the capillary tube assembly 100 is mounted, and the lumbar puncture needle 200" is described elsewhere herein in detail.

A clinician, wanting to diagnose normal pressure hydrocephalus (NPH) using conventional techniques, will employ two lumbar puncture needles each inserted into the spinal lumbar cavity. One needle is used to inject a liquid medium (e.g. water) into the cavity while the second needle, attached to a pressure gauge, is employed to measure hydrostatic pressure in the cavity which corresponds to the intracranial pressure (ICP). Alternatively, measurement of the ICP may be performed using a single large diameter needle for both infusion and measurement. As explained elsewhere, the use of two needles or a larger needle leads to patient discomfort and an increased risk of side-effects. The use of a single fine needle (e.g. about 20 G or 0.9 mm) and a gauge attached to a three way valve at the proximal end of the fine needle would severely overestimate the ICP. It is important that the ICP is measured reliably to allow the correct determination of the ICP as a function of the infusion rate, since this ratio has an important diagnostic value.

By employing the capillary tube assembly 100 inserted into the needle used to inject liquid medium, a more accurate estimate of ICP is obtained. Moreover, the procedure requires the use only of a single lumbar puncture needle for diagnosis of NPH.

The capillary tube assembly 100 provides an economical solution to these problems, that can be deployed on existing invasive tube assemblies (e.g. multilumen catheter, lumbar puncture needle) without significant adaptation.

Figure 6:
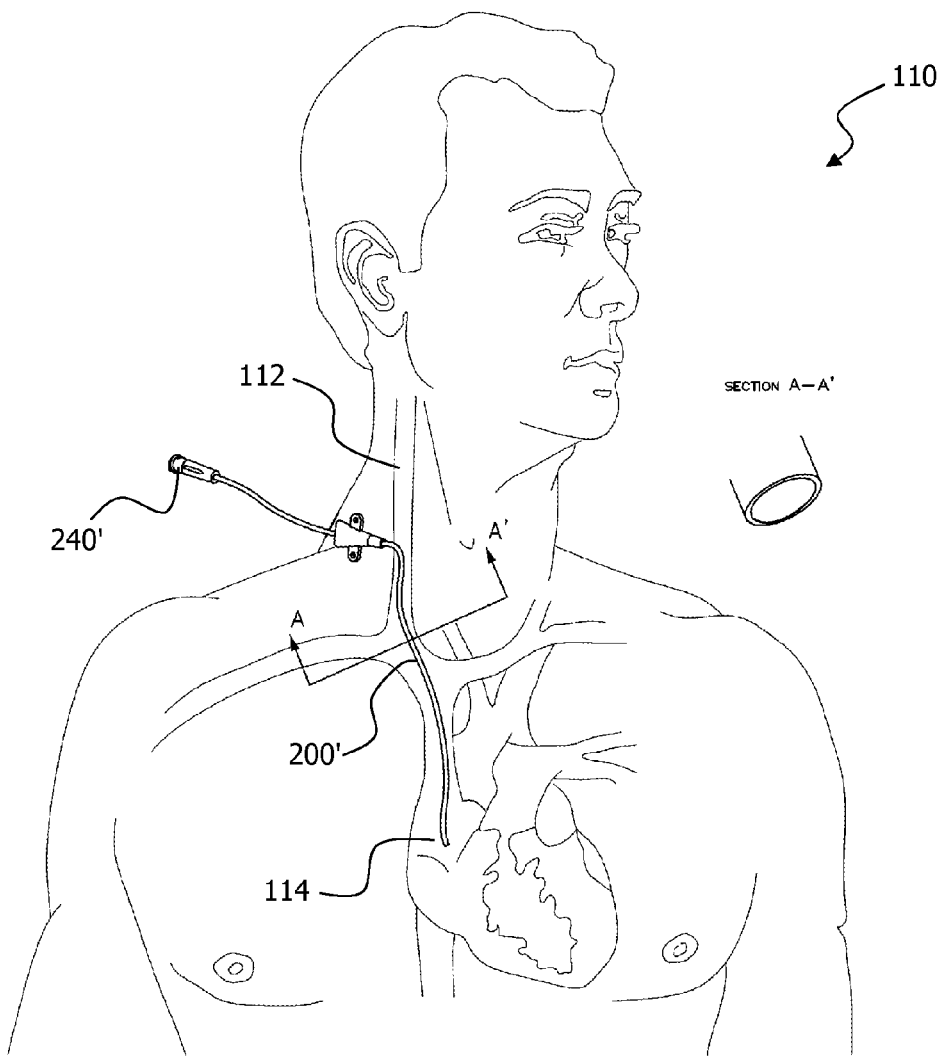
FIG. 6 depicts a single lumen catheter of the art in-situ in a subject; inset is a view of a transverse section across the catheter at line B-B'.
Figure 7:
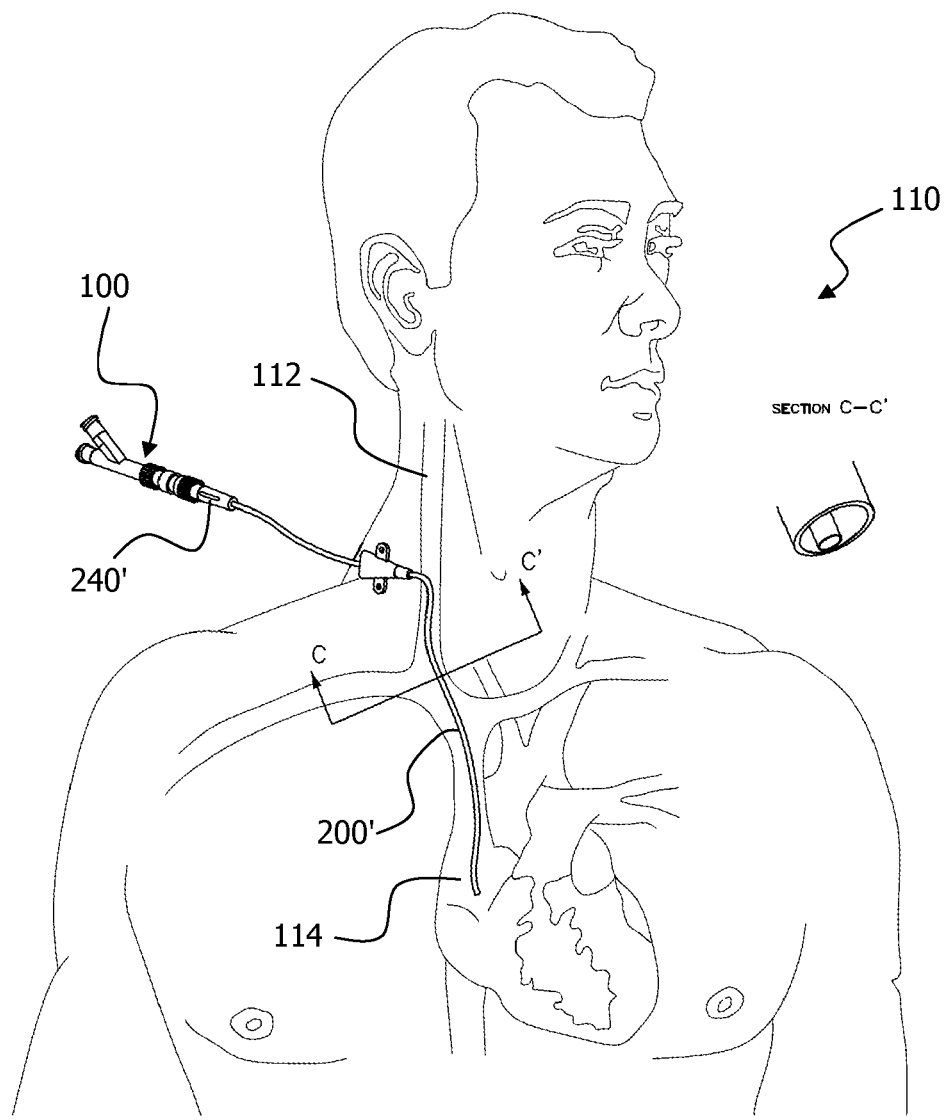
FIG. 7 depicts a single lumen catheter of FIG. 6 adapted using a catheter tube assembly of the invention; inset is a view of a transverse section across the catheter at line B-B'.
Figure 8:
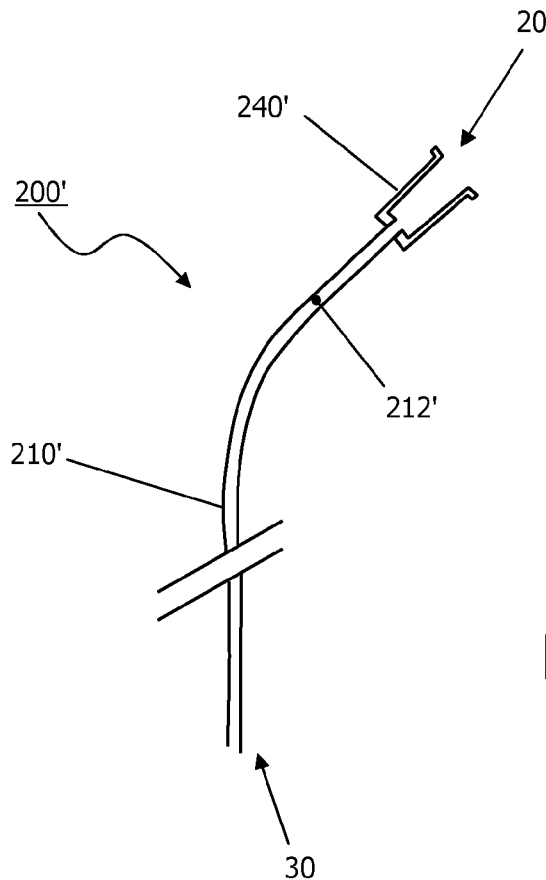
FIG. 8 depicts a cross-sectional view in a plane parallel to the longitudinal direction of a bodily invasive tube that is a catheter.
Figure 10:
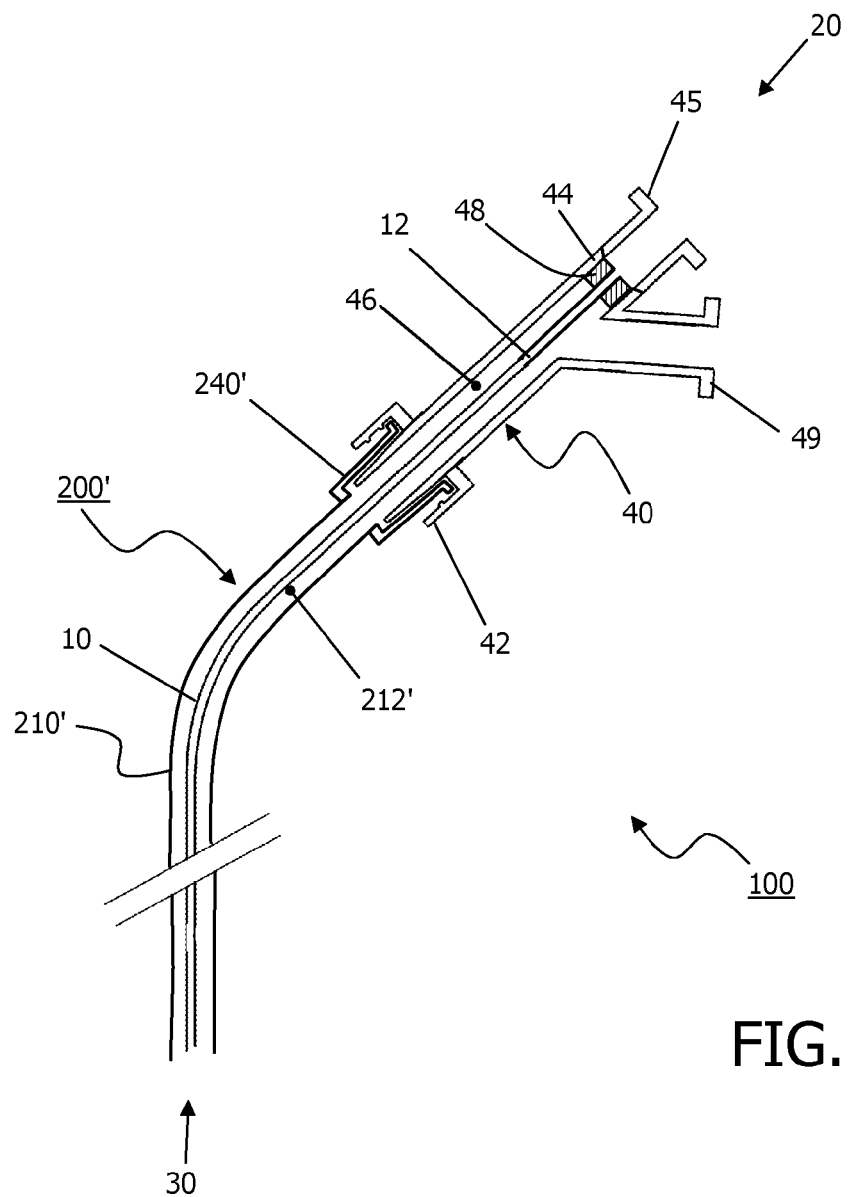
FIG. 10 depicts a cross-sectional view in a plane parallel to the longitudinal direction of a catheter tube assembly inserted into and connected with a bodily invasive tube that is a catheter.

The capillary tube assembly 100 may be employed with an invasive tube 200 that is a single or multichannel catheter, to provide said catheter with an additional channel when required (i.e. by dismountably inserting said capillary tube assembly 100), or to remove a channel when it is no longer required (i.e. by removing said capillary tube assembly 100 from mounting on the catheter). A subject 110 in which a single lumen catheter 200' has been inserted through the jugular vein 112 into the right atrium 114 of the heart is depicted in FIG. 6. FIG. 7 depicts the single lumen catheter 200' having been converted in situ into a two-lumen catheter using the capillary tube assembly 100 of the invention. An exemplary single lumen catheter 200' is shown in FIG. 8, FIG. 10 depicts said catheter 200' onto which the capillary tube assembly 100 is mounted, and the catheter 200' is described elsewhere herein in detail.

This advantageously provides multichannel access while requiring the use of a less rigid single lumen catheter, since additional fixed channels generally add to catheter rigidity. A more flexible catheter reduces endothelium damage and consequently thrombosis and emboli. Moreover, single lumen catheters have a more advantageous cross-sectional area for a given outer diameter, which is important when a high rate of fluid administration is required.

Conventional methods of swapping a single lumen catheter for a multi-lumen catheter entail risk—the existing catheter is most commonly removed on a guidewire, and the replacement catheter is fed on the same guidewire to the location of the previous catheter. The handling of a second catheter leads to an increased risk of infection, is labour intensive and highly uncomfortable for the patient. Infection especially presents a risk to patients having weakened immunity. Where the risk of infection is anticipated, the practitioner may enter via an entirely new puncture, however, the procedure is traumatic and can give rise to complications such as pneumothorax, hematothorax, nerve damage, accidental puncture of arteries, and stroke. By contrast, the present invention utilises the catheter in situ and provides at least one additional independent channel without disturbance to the existing catheter or the need for a new puncture. Thus, substantial intervention on the body is avoided. There is no substantial risk to health in view that it entails merely the insertion of the device of the invention into an existing tube, rather than through a bodily lumen. Moreover, it can be carried out by a non-surgeon, such as a nurse.

Thus, when the clinician decides it is necessary, the in situ catheter can be adapted, that is to say provided with one or more additional lumens using the capillary tube assembly, or vice versa. The straightforward conversion from a single-lumen to a multi-lumen or vice versa catheter decreases the number of manipulations, increases patient comfort, reduces infection risk, and risk of other complications. The cost of the procedure is also reduced because the need for the more expensive multilumen catheters is obviated, and more importantly, the time-consuming procedure of catheter replacement is avoided.

In practice, the clinician will insert a multilumen catheter into a patient before the start of an operation, which patient is then transferred to intensive care or directly to the ward. Additionally, most patients that are treated in intensive care units will receive a multilumen catheter, and eventually are transferred to the ward. In both cases, the multilumen catheter is typically replaced by a single-lumen prior to transfer to the ward, because the presence of unused lumens hold a risk of infection and thrombosis which are life-threatening complications, and it is highly uncomfortable for the patient. However, replacement entails the aforementioned risks. This additional step of catheter replacement could be avoided using the present invention.

The outside of any catheter is soft in order to be minimally traumatic in respect of endothelium damage due to insertion and cardiac pulsations. Classical multichannel catheters are made from a solid tube of single material, into which individual channels are introduced. As a result, the internal channel walls are relatively thick, and the catheter is stiffer compared with a single lumen device. Moreover, there is a loss of useful lumen area.

The present invention allows for the introduction of a soft and flexible single lumen, that can be later upgraded to a multi-lumen catheter using stiffer materials. Since the initial catheter (invasive tube) is generally single lumen, it may be soft and, therefore, avoids trauma to the endothelium. Any rigidity of the later-inserted capillary tube will not cause damage the endothelium because it is introduced within the lumen of the initial catheter. The invention thus provides a different material choice for the internal lumens and external catheters. This allows for optimal use of soft material for the outer catheter, and the use of ultrathin walled rigid material for the internal capillary system.

The use of different material for the additional lumen has a further advantage in that the capillary tube may be optimized for pressure measurements. For optimal transduction of a pressure change, rigid tubing material is preferred.

A further use of requirement for multichannel catheters is the necessity to have a lumen that is exclusively used for a particular drug. Because of the high pharmacological activity and short half-life of certain drugs (for instance adrenaline), it is critical that its administration is uninterrupted and constant. If the drug would be administered through the main catheter channel, an interruption of the flow due to an empty fluid canister or a kink, the interruption of the drug administration and the subsequent overdose of drug after restoration of the fluid flow would be unacceptable. Secondly, when using a dedicated lumen for the drug, changes in drug administration have immediate pharmacological effect, while mixing it with the main channel may delay its effect. Another reason for administering drugs in separate channels is pharmacological incompatibility, which means certain drugs can not be mixed before dilution in the blood. The fluidically separated channels that the present invention provides allow for simultaneous administration of pharmacologically incompatible drugs, particularly in cases where the requirement for an additional channel for administration was not envisaged when the catheter was initially inserted.

Figure 12A:
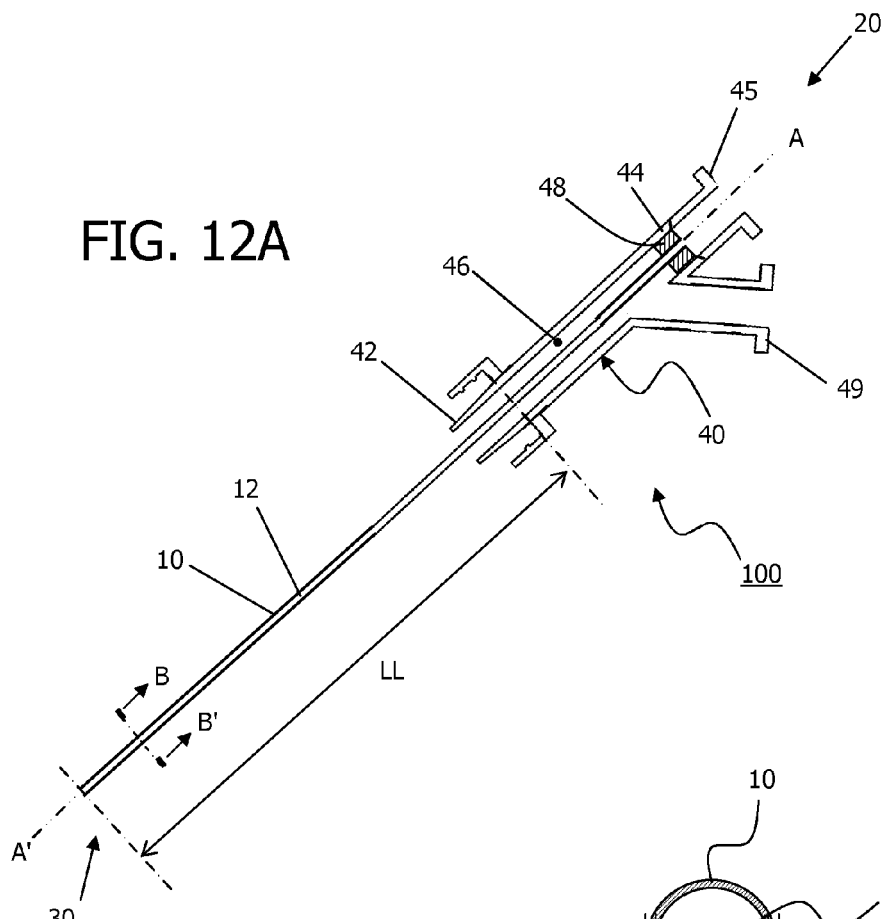
FIG. 12A depicts a cross-sectional view in a plane parallel to the longitudinal direction of a catheter tube assembly provided with a Y-shaped, Luer type adapter, with dimensions indicated.

The capillary tube shaft 10 of the assembly 100 has an open distal 30 end and an open proximal 20 end, and disposed within the shaft 10 is at least one lumen 12 configured for the passage of fluid. The number of capillary tube lumens may be 1, 2, 3, 4, 5, or 6 or more. Each lumen 12 connects the open distal 30 end of the shaft 10 with the open proximal 20 end. When there is more than one lumen, they are in fluidic isolation from each other within the shaft 10. The capillary tube shaft assembly 100 has a longitudinal axis (A'-A) as shown in FIG. 12A; the longitudinal axis becomes most apparent when the capillary tube shaft 10 is linear.

The capillary tube shaft 10 of the assembly 100 is configured for advancement through the invasive tube lumen. More in particular, the capillary tube shaft 10 is adapted for dismountable insertion from its distal 30 end, into the proximal 20 end of the invasive tube lumen 212. FIG. 10 depicts a capillary tube shaft 10 inserted into the lumen 212 of an invasive tube, when said invasive tube is a catheter 200'. FIG. 11 depicts a capillary tube shaft 10 inserted into the lumen 212 of an invasive tube 200, when said invasive tube is a lumbar puncture needle 200". As such capillary tube shaft 10 is flexible, but stiffened to provide pushability through the lumen 212 without kinking or buckling. In other words, the capillary tube shaft 10 is kink resistant. It should also have good trackability, and tensile strength so as not to damage upon withdrawal. Typically the capillary tube shaft 10 has a cylindrical transverse sectional profile, though other profiles are not excluded such as ovoid or polygonal.

Figure 12B:
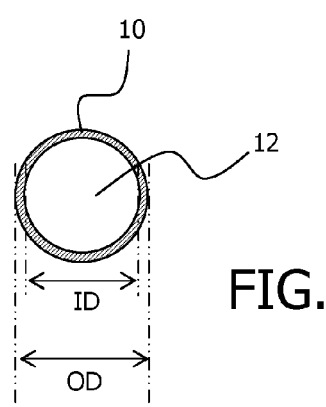
FIG. 12B depicts a transverse cross section of a catheter of FIG. 12A across the line B-B'.

As shown in FIG. 12B depicting a transverse (A-A') cross-section of the capillary tube shaft 10, the outer wall of the capillary tube shaft 10 is complete and intact along the length, to provide a fluid impermeable passage that facilitates transport of fluid along the lumen 12.

The length of the capillary tube shaft 10 is such that the distal tip is able to advance through an invasive tube lumen 212 towards the distal 30 tip of the invasive tube 200. Preferably, the length is such that the capillary tube shaft 10 distal tip is in a recessed or flush position relative to the distal 30 tip of the invasive tube 200, particularly when the adapter 40 of the assembly 100 is connected to the coupling 240 of the invasive tube 200. While a recessed or flush juxtaposition is preferred, it is within the scope of the invention that the length of the capillary tube shaft 10 allows it to protrude relative to the distal 30 tip of the invasive tube 200, for example, by 1, 2 or 3 mm. It will be appreciated that the length of the protrusion is minimised to avoid a risk of damaging the tissue under intervention.

The luminal length, LL (FIG. 12A) of the capillary tube shaft 10, which is the linear distance between the adapter 40 and the distal 30 tip of the capillary tube shaft 10, may be equal to, or less than, or more than the length of the invasive tube shaft 210. The luminal length, LL may be adjustable, for instance, by employing an adapter 40 in sliding relation to the elongated member 10, or by truncation of the capillary tube shaft 10 from the distal 30 end. Where the capillary tube shaft 10 protrudes from the distal 30 tip of the invasive tube 200, the tip of the capillary tube shaft 10 may be softened, for example, made from a flexible material.

As a general guidance, the luminal length, LL (FIG. 12A) of the capillary tube shaft 10 between the adapter 40 and the distal 30 tip may be equal to or less than 120%, 110%, 105%, 99%, 98%, 96%, 94%, 92%, 90%, 85%, 80%, 75% of the length of the invasive tube 200, or a value between any two of the aforementioned values.

In situ coupled to the invasive tube 200, the distal tip may be in a flush or recessed configuration relative to the distal 30 tip of the invasive tube 200. The distal tip of the capillary tube shaft 10 may be at a distance of 0 mm, 0.1 mm, 0.2 mm, 0.4 mm, 0.6 mm, 1 mm, 2 mm, 3 mm, 4 mm, 6 mm, 8 mm, or 10 mm proximal to the distal tip of the invasive tube 200.

In situ coupled to the invasive tube 200, the distal tip may protrude relative to the distal 30 tip of the invasive tube 200. The distal tip of the capillary tube shaft 10 may protrude by a distance of 0 mm, 0.1 mm, 0.2 mm, 0.4 mm, 0.6 mm, 1 mm, 2 mm, 3 mm, 4 mm, 6 mm, 8 mm, or 10 mm proximal to the distal tip of the invasive tube 200.

The maximum outer diameter OD (FIG. 12B) of the capillary tube shaft 10 is smaller than the inner diameter of the invasive tube 200 lumen 212. Additionally, it is configured to substantially maintain the flow functioning of the invasive tube lumen 212 i.e. the flow of fluid through the invasive tube lumen 212 is not substantially hindered when the capillary tube shaft 10 is deployed in the tube. According to one embodiment of the invention, the maximum outer diameter OD (FIG. 12B) of the capillary tube shaft 10 is equal to or less than 5%, 10%, 20%, 30%, 40%, 50%, 60%, or 70% of the inner diameter of the invasive tube lumen 212, or a value between any two of the aforementioned values, preferably between 5% and 50%. As a general guidance, the OD of the capillary shaft may be 0.2 mm, 0.3 mm, 0.4 mm, 0.5 mm, 0.6 mm, 0.7 mm, 0.8 mm, 0.9 mm or a value in the range between any two of the aforementioned values, preferably between 0.2 mm and 0.6 mm, preferably around 0.4 mm; this is particularly applicable when the inner diameter of the invasive lumen is 1.67 mm.

Whether the flow of fluid through the invasive tube lumen 212 is not substantially hindered when the capillary tube shaft 10 is deployed in the invasive tube can be determined by flow rate tests. The fluid flow rate in the invasive tube lumen 212 is measured at constant pressure without and with the capillary tube shaft 10 deployed therein. Should the flow rate drop by a certain amount, then the capillary tube shaft 10 may play a substantially hindering role. Typically, the flow functioning of the invasive tube lumen 212 is maintained when the fluid flow at constant pressure is reduced by 0%, or an amount equal to or less than 5%, 10%, 20%, 30%, 40%, 50%, 60% when the assembly is coupled to the invasive tube, more particularly, when the capillary tube shaft 10 is deployed therein compared to when it is absent.

The skilled person will appreciate that the thickness of the wall of the capillary tube shaft 10 will depend on several factors including the material used, the outer diameter and length of the capillary tube shaft, and would understand how to determine the optimum thickness. However, the capillary tube shaft is thin walled. As a general guidance, the thickness of the wall may be equal to or less than 0.01 mm, 0.02 mm, 0.03 mm, 0.04 mm, 0.05 mm 0.06 mm 0.07 mm, 0.08 mm, 0.1 mm, 0.2 mm, 0.3 mm, 0.4 mm, or 0.5 mm or a value in the range between any two of the aforementioned values, preferably between 0.02 mm and 0.3 mm, more preferably between 0.02 and 0.07 mm, preferably around 0.05 mm.

In a preferred aspect of the invention the capillary tube shaft has an external diameter of 0.2 mm to 0.6 mm, and a wall thickness of 0.02 mm to 0.07 mm.

The capillary tube shaft may be formed from any suitable material that forms a narrow walled capillary tube that has pushability and tractability, is flexible and kink resistant, has requisite column strength and tensile strength and is chemically inert. The capillary tube shaft may be formed at least partly, preferably entirely from polyimide. The capillary tube shaft may be provided with or without a stainless steel braid. An example of a suitable capillary tube shaft is the thin walled polyimide catheter (Microlumen, Tampa, Fla.) provided with or without a stainless steel braid. In case of a protruding tip, more flexible material such as Pebax can be used at the distal end.

The proximal 20 end or portion of the capillary tube shaft 10 is provided with an adapter 40 configured to provide independent fluidic access to each lumen of the capillary tube shaft 10. The body (outer wall) of the proximal 20 end or portion of the capillary tube shaft 10 is preferably sealably connected to the adapter 40. The adapter 40 also allows dismountable connection to a reciprocating coupling 240 on the proximal end of the invasive tube 200. The adapter 40 is configured to fluidicly isolate the capillary lumen 12 from the invasive tube lumen 212. More in particular, the adapter 40 is configured to fluidicly isolate the open proximal 20 end of the capillary tube shaft 10 from the open proximal end 20 of the invasive tube 200.

The adapter 40 is positioned substantially in the proximal 20 half, or at the proximal end of the capillary tube shaft 10. As exemplified in FIG. 2, the adapter 40 preferably has an essentially longitudinal shape, a proximal 20 and distal 30 end. The distal end 30 is preferably configured for attachment to the coupling 214 of the invasive tube 200. The proximal end 20 is preferably provided with a connector 45 for attachment to a reciprocating connector, providing exclusive access to the capillary tube lumen 12. A side port may provide exclusive access to the invasive tube lumen 212. The connector 45 may be a female Luer lock connector i.e. a female Luer push connector around which a male thread is disposed. The adapter 40 is provided with a fluid-tight internal chamber 46. The adapter 40 is disposed around the capillary tube shaft 10, in a collar-like arrangement; the respective longitudinal axes may be aligned essentially co-axially.

At the distal end 30 of the adapter 40 is an open connector 42 in fluidic connection with the chamber 46, adapted to engage with the coupling 240 of the invasive tube 200, or to an intermediate coupling connected to the coupling 240 of the invasive tube 200. FIG. 10 depicts a capillary tube adapter 40 fluidicly connected into the coupling 240 of an invasive tube, when said tube is a catheter 200'. FIG. 11 depicts a capillary tube adapter 40 fluidically connected into the coupling 240 of an invasive tube, when said tube is a lumbar puncture needle 200". The capillary tube shaft 10 is disposed through this open connector 42.

The connector 42 is preferably essentially tubular, hollow and threaded; more preferably it comprises a male Luer lock connector i.e. a male Luer push connector in concentric alignment with an outer female screw thread which may be independently rotating. It will be appreciated that the adapter coupling 42 may equally be a connector other than Luer lock connector. For example, it may be a custom-made connector, configured to connect with a reciprocating connector 240 on the bodily invasive tube 200. The custom-made connector and its reciprocating pair may be available in a variety of different configurations, whereby a particular connector configuration dismountably attaches only to its specific and complementary reciprocating pair, and not to another coupling linked with another bodily invasive tube 200 size. This prevents a capillary tube assembly 100 from connecting to an inappropriate invasive tube 200. It is envisaged that different sizes of capillary tube assembly 100, each suitable for a different invasive tube 200 may be made available, and the user can determine that the capillary tube assembly 100 and invasive tube 200 are compatible by virtue of achieving proper coupling.

The adapter 40 is also provided with a proximal port 44. The proximal port 44 is positioned toward the proximal 20 end of the adapter 40. Preferably, a central axis of the port 44 is in co-axial alignment with a central axis of the connector 42.

The body of the proximal 20 portion or end of the capillary tube shaft 10 may be disposed through the proximal port 44. The proximal port 44 is fluidically sealed around the outer body of the capillary tube shaft 10. This may be achieved using, for example, a plug 48 of silicone or rubberized polymeric resin molded around the outer body of the capillary tube shaft 10. When mounted on the invasive tube 200, the chamber 46 of the adapter 40 is in sealed fluidic connection with one of the invasive tube 200 lumens 212. Since the proximal end or part of the capillary tube shaft 10 passes through the proximal port 44 and the proximal port 44 is sealed there around, the chamber 46 is fluidicly isolated from the proximal 20 end of the capillary tube shaft 10. The proximal port 46 may be extended proximally 20 to include a connector 45 for dismountable attachment to a reciprocating connector; the reciprocating connector may be operatively attached to an external device such as a pressure gauge. The connector may be, for example, a Luer connector for dismountable attachment to a pressure gauge. Preferably, the connector 45 is a female Luer lock connector i.e. a female Luer push connector around which a male thread is disposed.

The embodiment shown in FIG. 2 depicts an adapter 40 devoid of a side port, which is not required when the coupling 240 on the invasive tube 200 is connected to an intermediate coupling (not shown) provided with a side port or valve allowing access to the invasive tube 200 lumen 212.

An intermediate coupling is an inline connector configured to join fluidicly the adapter 40 of the capillary tube assembly 100, more preferably the open connector 42 thereof, to the coupling 240 of the invasive tube 200. It may be disposed with a side port for fluidic access to the invasive tube lumen 212. The side port may be, for example, a Luer connector. Preferably, the side port may be a female Luer lock connector i.e. a female Luer push connector around which a male thread is disposed. Preferably, the intermediate coupling is dismountable. Examples of intermediate couplings are a Y Connector, 4-Way Connector, 5-Way Connector, 6-Way Connector and the like.

Alternatively, however, the adapter 40 may further be provided with a side port 49 in fluid connection with the chamber 46 and hence the distal open connector 42 as exemplified in FIG. 3. The side port 49 is positioned between the distal connector 42 and the proximal port 44. When mounted on the invasive tube 200, the chamber 46 of the coupling 40 is in sealed fluidic connection with the invasive tube lumen 212 and the side port 49 allows access to the invasive tube lumen 212, permitting the introduction of rinse fluid.

It is within the scope of the invention that the capillary tube shaft 10 passes either through the proximal port 44 as exemplified in FIGS. 2 and 3 and as explained above, or through the side port 49. Where it passes through and is sealed against the side port 49, the proximal port 44, rather than the side port 49 allows access to the rinse inlet lumen 234, permitting the introduction of rinse fluid.

The adapter 40 may be provided in slidable or fixed relation to the capillary tube shaft 10.

When it is in fixed relation, the capillary tube shaft 10 may be trimmed from the distal end so as to adjust its luminal length LL according to the length of the invasive tube shaft 210. When it is in sliding relation, it is not necessary to truncate the capillary tube shaft 10, to match the length of the invasive tube shaft 210; the desired luminal length LL can be achieved by sliding the adapter 40 relative to the body of the capillary tube shaft 10. The adapter 40 may be provided in fixed relation by utilizing the sealing plug 48 of rubberized or silicone material to frictionally or adhesively engage with the outer wall of the capillary tube shaft 10. The coupling may be provided in lockable, slidable relation by utilizing the plug 48 of rubberized or silicone material as a sliding seal that engages with a friction-reduced (e.g. Teflon coated) outer wall of the capillary tube shaft 10. It may be locked by any means, such as a locking pin or screw.

Preferably, the adapter 40 is a standard three-branch, Y-shaped hub, two branches of the hub each provided with a female Luer lock connector i.e. a female Luer push connector around which a male thread is disposed, and one branch of the hub provided with a male Luer lock connector i.e. male Luer push-fitting about which a female threaded collar is provided that is optionally independently rotating. The latter branch typically connects to the coupling 240 of the invasive tube 200.

With reference to FIG. 5, the invasive tube 200 into which capillary tube assembly 100 can be dismountably inserted, comprises a hollow longitudinal shaft 210 (invasive tube shaft) having an open distal 30 end and an open proximal 20 end, and disposed within the shaft 210 is at least one lumen 212 configured for the passage of fluid. The number of invasive tube lumens may be 1, 2, 3, 4, 5, or 6 or more; the invasive tube 200 shown in FIG. 5 has a single lumen 212. Each lumen 212 connects the open distal 30 end of the invasive tube shaft 210 with the open proximal 20 end. When there is more than one lumen, they are in fluidic isolation within the invasive tube shaft 210. The shaft 210 may be formed from a single tube, or from a plurality of tubes tandemly joined to provide continuity of the lumen or lumens 212. The invasive tube 200 has a longitudinal axis (A'-A) as shown in FIG. 5; the longitudinal axis becomes most apparent when the invasive tube shaft 210 is linear.

The proximal 20 end of the invasive tube shaft 210 may be provided with a coupling 240, configured for dismountable attachment to the adapter 40 of the assembly 100. The coupling is also configured for fluidic access to the invasive tube lumen 212. The coupling 240 is in fluidic connection with the invasive tube lumen 212. When there is more than one lumen, there may be one coupling per lumen. The coupling 240 may comprise a female Luer lock connector i.e. a female Luer push connector around which a male thread is disposed (illustrated in FIG. 5). The coupling may further comprise a side port (not shown) configured for fluidic access to the invasive tube lumen 212; this side port may comprise a female Luer lock connector i.e. a female Luer push connector around which a male thread is disposed. Access to the invasive tube lumen 212 may be provided using one or more separate intermediate couplings provided with a side-port as described elsewhere herein.

Said access is independent from the access to the one or more lumens 12 of the capillary tube assembly 100. The number of couplings 240 may be the same as the number of lumens present in the invasive tube shaft 210. There may be one coupling for each lumen. Thus, a single lumen invasive tube may be provided with a single coupling, a two lumen invasive tube may be provided with two couplings, a three lumen invasive tube may be provided with three couplings etc.

The invasive tube 200 is configured for insertion into a bodily cavity. Examples of a bodily cavity include a blood vessel, preferably a vein, more preferably a central venous vessel. It also includes a lumbar cavity, and bladder. The invasive tube may enter through skin or via an externally connected duct (e.g. urethra).

The invasive tube 200 may be a single channel catheter 200' (e.g. FIG. 8) provided with a catheter lumen 212' extending between the open distal 30 end and open proximal 20 end for conductance of a fluid. The invasive tube 200 may be a multi-channel catheter provided with two or more catheter lumens 212 (e.g. 2, 3, 4, 5, 6 or more catheter lumens) extending between the open distal 30 end and an open proximal 20 end for conductance of a fluid.

An exemplary catheter is depicted in FIG. 8, having a catheter shaft 210' that is open at the proximal 20 and distal 30 ends provided with a single catheter lumen 212 extending between the open distal 30 end and open proximal 20 end for conductance of a fluid. The outer wall of the catheter shaft 210' is complete and intact along the length, to provide a fluid impermeable passage that facilitates transport of fluid along the lumen 212'. The proximal end 20 of the catheter is provided with the coupling 240' configured for fluidic attachment to the adapter 240' of the capillary tube assembly 100, directly or via one or more intermediate couplings. The coupling 240' is also configured for fluidic access to the catheter lumen 212'.

The inner diameter, ID, of the catheter lumen 212' is configured to allow the passage of fluid without substantial hindrance when the capillary tube shaft 10 in inserted therein. According to one aspect of the invention, the minimum diameter of the catheter lumen 212' is equal to or no more than 10%, 20%, 30%, 40%, 50%, 60%, 70%, 75%, 80%, 90% greater than the outer diameter, OD, of the capillary tube shaft 10, or a value in the range between any two of the aforementioned values, preferably between 70% and 80%, most preferably 75%; the preferred values are particularly applicable when the OD of the capillary tube shaft 10 is 0.4 mm.

The wall of the catheter shaft 210' may be formed from any suitable non-expandable material such as polyurethane.

The catheter is preferably a venous catheter, more preferably a central venous catheter. It may be a central venous catheter having a French size of 9 or less, e.g. 8, 7, 6, 5, 4, 3, 2 or 1.

As mentioned elsewhere herein, the capillary tube assembly 100 may be utilised to measure pressure at the distal tip of the catheter, and/or utilised to adapt an existing catheter by providing an additional lumen, which adaptation can later be reversed when the additional lumen is no longer required.

The catheter coupling 240' preferably comprises a female Luer lock connector i.e. a female Luer push connector around which a male thread is disposed. The coupling may further comprise a side port (not shown) configured for fluidic access to the catheter lumen 212; this side port may comprise a female Luer lock connector i.e. a female Luer push connector around which a male thread is disposed. Access to the catheter lumen 212 may be provided using one or more separate intermediate couplings provided with a side-port as described elsewhere herein.

It will be appreciated that the catheter coupling 240' may equally be a connector other than Luer lock connector. For example, it may be a custom-made connector, configured to connect with a reciprocating connector on the adapter 40 or intermediate coupling 520. The custom-made connector and its reciprocating pair may be available in a variety of different configurations, whereby a particular connector configuration dismountable attaches only to its specific and complementary reciprocating pair, and not to another coupling. This prevents a capillary tube assembly 100 from connecting to an inappropriate invasive tube 200. It is envisaged that different sizes of capillary tube assembly 100, each suitable for a different invasive tube 200 may be made available, and the user can determine that the capillary tube assembly 100 and invasive tube 200 are compatible by virtue of achieving coupling.

The invasive tube 200 may be a lumbar puncture needle. A lumber puncture needle 200", known in the art, and an exemplary device is shown in FIG. 9. It has a proximal 20 and distal end 30. It a typically comprises a shaft 210" that is optionally rigid, and disposed within the shaft 210" is a lumen 212" that extends from an open distal end 30 to an open proximal 20 end for conductance of a fluid. The open distal 30 end is sharpened (pointed) for piercing the skin and other tissues. Attached to the proximal end 20 and in fluid connection with the lumen is a coupling 240", configured for attachment to the adapter 40 of the capillary tube assembly 100.

The lumbar puncture needle may be a single channel needle (illustrated in FIG. 9) or a multi-channel needle provided with two or more needle lumens 212" (e.g. 2, 3, 4, 5, 6 needle lumens) extending between the open distal end and an open proximal 20 end for conductance of a fluid.

The inner diameter, ID, of the needle lumen 212" is sufficient to allow the passage of fluid without substantial hindrance when the capillary tube shaft 10 in inserted therein. According to one aspect of the invention, the minimum inner diameter of the needle lumen 212" is equal to or no more than 10%, 20%, 30%, 40%, 50%, 60%, 70%, 75%, 80%, 90%, 100%, 110%, 120% greater than the outer diameter, OD, of the capillary tube shaft 10, or a value in the range between any two of the aforementioned values, preferably between 70% and 120%, most preferably 100%; the preferred values are particularly applicable when the OD of the capillary tube shaft 10 is 0.3 mm.

The inner diameter, ID, of the lumber puncture needle 212" may be equal to or more than 0.9 mm, 0.8 mm, 0.85 mm, 0.7 mm, 0.6 mm, 0.5 mm, 0.4 mm or a value in the range between any two of the aforementioned values, preferably 0.5 mm to 0.7 mm.

The outer diameter of the lumber puncture needle 212" may be equal to or more than 0.8 mm, 0.9 mm, 1 mm, 1.1 mm, 1.2 mm, 1.3 mm or a value in the range between any two of the aforementioned values, preferably 0.8 mm to 1 mm. Preferably it is a 20 G needle. The wall of the needle shaft 212" may be formed from any suitable non-expandable material such as stainless steel.

The needle coupling 240" is preferably comprises a female Luer lock connector i.e. a female Luer push connector around which a male thread is disposed. The coupling may further comprise a side port (not shown) configured for fluidic access to the needle lumen 212"; this side port may comprise a female Luer lock connector i.e. a female Luer push connector around which a male thread is disposed. Access to the needle lumen 212" may be provided using one or more separate intermediate coupling provided with a side-port as described elsewhere herein.

As mentioned elsewhere herein, the capillary tube assembly 100 may be utilised to measure pressure at the distal tip of the needle.

Introduction of a capillary tube shaft 10 into an invasive tube 200 such as venous catheter or central venous catheter and fixation of the adaptor 40 to the coupling 240 of such invasive tube 200 is ideally performed under sterile conditions to prevent infections. It may be challenging for a practitioner to introduce the flexible capillary tube shaft 10 into the proximal part of the invasive tube coupling 240 without touching the sterile parts.

Accordingly, another embodiment of the invention is an applicator package 500, comprising the capillary tube assembly 100 as described herein and an applicator 510. A further embodiment relates to the applicator 510. The applicator 510 and applicator package 500 allow the sterile introduction of the capillary tube shaft 10 into the invasive tube 200 lumen 212.

Figure 13:
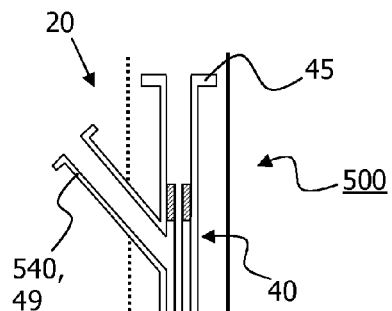
FIG. 13 depicts a cross-sectional view in a plane parallel to the longitudinal direction of an applicator of the invention that comprises a protective rigid tube, in which the adapter is provided with a side port. A catheter tube assembly is disposed in the applicator.

With references to FIGS. 13 to 36, the applicator package 500 comprises a capillary tube assembly 100 as described herein and a protective cover 560 that at least partly covers the capillary tube assembly 100 and allows the capillary tube assembly 100 to slide longitudinally within a void 568 of the cover 560. The protective cover maintains the capillary tube assembly 100 in a sterile environment. The applicator may further comprise an opening at the distal end 30 which may be sealed with a detachable seal (585, FIG. 37; 585' 38), or may be disposed with the intermediate coupling 520 mounted over the capillary tube shaft 10 (FIG. 13). The protective cover 560 allows the capillary tube assembly 100 to slide longitudinally relative to the opening at the distal end that has a detachable seal 585, 585' or intermediate coupling 520. Where an intermediate coupling 520 is present, the capillary tube shaft 10 is preferabled slidably mounted through the intermediate coupling 520.

Figure 15:
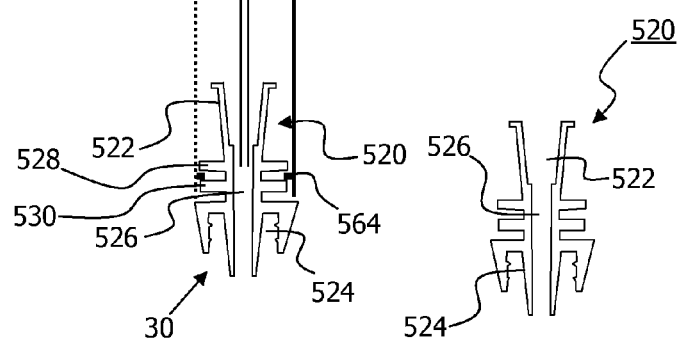
FIG. 15 depicts a cross-sectional view in a plane parallel to the longitudinal direction of an intermediate coupling devoid of a side port.
Figure 16:
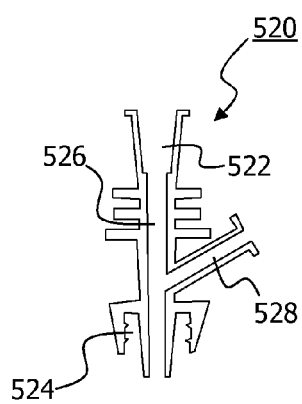
FIG. 16 depicts a cross-sectional view in a plane parallel to the longitudinal direction of an intermediate coupling provided with a side port.
Figure 13A:
FIG. 13A depicts a transverse cross-sectional view of an applicator of the invention across the line D-D' of FIG. 13.

As explained elsewhere herein, an intermediate coupling 520 is an inline connector having a proximal 20 and distal 30 end. It is configured to connect fluidicly to the proximal 20 end of the adapter 40 of the capillary tube assembly 100, more preferably the open connector 42 thereof, and to the coupling 240 of the invasive tube 200 at its distal 30 end. With reference to FIGS. 15 and 16, the intermediate coupling 520 is disposed with a fluidic coupling 522 at its proximal 20 end configured for attachment to the adapter 40 of the capillary tube assembly 100. Such coupling 522 is preferably a female Luer lock connector i.e. a female Luer push connector around which a male thread is disposed.

It is also disposed with a fluidic coupling 524 at its distal 30 end configured for attachment to the coupling 240 of the invasive tube 200. Such coupling 524 is preferably a male Luer lock connector i.e. a male Luer push connector in concentric alignment with an outer female screw thread. Preferably said outer female screw thread is not independently rotatable. It will be appreciated that the distal fluidic coupling 524 may equally be a connector other than Luer lock connector. For example, it may be a custom-made connector, configured to connect with a reciprocating connector 240 on the bodily invasive tube 200. The custom-made connector and its reciprocating pair may be available in a variety of different configurations, whereby a particular connector configuration dismountably attaches only to its specific and complementary reciprocating pair, and not to another coupling. This prevents a capillary tube assembly 100 from connecting to an inappropriate invasive tube 200. It is envisaged that different sizes of capillary tube assembly 100 and intermediate coupling 520 each suitable for a different invasive tube 200 may be made available, and the user can determine that the capillary tube assembly 100 and invasive tube 200 are compatible by virtue of achieving proper coupling.

The fludic couplings 522, 524 at the proximal 20 and distal 30 ends of the intermediate coupling 520 are each fluidicly joined to a chamber 526 disposed within the body of the intermediate coupling 520. Fluid flowing between the proximal 20 and distal 30 fluidic couplings 522, 524 thus pass through said chamber 526. The intermediate coupling 520 may be disposed with a side port 528 (FIG. 16) for fluidic access to the chamber 526 of the intermediate coupling. When the intermediate coupling 520 is connected to the invasive tube, the side port 528 provides fluidic access to the invasive tube lumen 212. The side port 528 may be, for example, a Luer connector. Preferably, the side port 528 may be a female Luer lock connector i.e. a female Luer push connector around which a male thread is disposed. Preferably, the intermediate coupling is dismountable. Examples of intermediate couplings are a Y Connector, 4-Way Connector, 5-Way Connector, 6-Way Connector.

As mentioned elsewhere herein, the protective cover 560 may be provided with an opening at the distal end that is sealed with a detachable seal 585, 585' (FIGS. 37, 38). The is preferably when then intermediate coupling 520 is absent. Preferably the protective cover at the distal end 30 comprises a conical or pointed tip 587, 587' which incorporates the detachable seal 585, 585'. When the seal is removed, the tip retains truncated a conical or pointed portion. The conical or pointed tip allows alignment of the applicator 510 within the coupling 240 of the invasive tube 200. The seal may be removed by means of a weakened joint 586, 586', or can be removed by cutting.

The protective cover 560 comprises a covering that encloses at least partly the capillary tube assembly 100 and the intermediate coupling 520 where utilised. The covering may be rigid (e.g. a tube) or flexible (e.g. a foil pouch, bellows tube). The protective cover 560 maintains in a sterile condition the components that come into contact with the body. It generally has a longitudinal shape, and a proximal 20 and distal end 30. The protective cover 560 has an interior void 568 in which the capillary tube assembly 100 and the intermediate coupling 520 where utilised are disposed in a sterile condition. The proximal end of the capillary tube assembly 100 is aligned with the proximal end of the protective cover 560. The distal end of the capillary tube assembly 100 is aligned with the distal end of the protective cover 560.

The distal end 30 of the protective cover 560 may be provided with an opening in which the intermediate coupling 520 is disposed and dismountably engaged. Alternatively, the distal end 30 of the protective cover 560 may have an open distal end 30 sealed with a detachable seal 585, 585', having a pointed, conical or funnel shape, enabling insertion into the coupling 240 of the invasive tube 200; the protective cover may be devoid of an intermediate coupling.

The proximal end 20 may be closed. Alternatively, the proximal end 20 of the protective cover 560 may be provided with an opening in which the adapter 40 is disposed and dismountably engaged.

Preferably, the open connector 42 at the distal end of the adapter 40, the capillary tube shaft 10, and the fluidic coupling 522 at the proximal end of the intermediate coupling 520 (where present) are disposed in the void 568. The connector 45 at the proximal end of the adapter 40, and/or the side port 49 of the adapter 40, and/or the fluidic coupling 524 at the distal end of the intermediate coupling 520 where utilised may not be covered; they may each be provided with a detachable plug. The plug maintains said connector 45, side port 49 and/or the fluidic coupling 524 in a sterile condition. The plug can be removed prior to use. Sterile condition may be achieved by irradiating. Irradiation is performed with protective cover, any plugs and the capillary tube assembly 100 in situ. The protective cover allows at least the capillary tube shaft 10 of the capillary tube assembly 100 to slide relative to the intermediate coupling 520 within the void 568.

According to one embodiment of the invention, the protective cover 560 is a protective tube 560' (FIG. 13) that covers the capillary tube assembly 100. The protective tube 560' is a longitudinal, hollow, rigid tube. The protective tube 560' may have an open distal end. The opening at the distal end 30 may be sealed with a detachable seal or with an intermediate coupling 520. The protective tube 560' may have an open or closed proximal end. The protective tube 560' may be cylindrical. It is disposed with a longitudinal breachable seal 562 that advances the longitudinal length of the wall of the protective tube, from the distal 30 end to the proximal 20 end. The longitudinal breachable seal 562 may be comprised in a thinned wall of the protective tube, in the abutting edges of a longitudinal slit in the wall, in the overlapping edges of a longitudinal slit in the wall, in a linear strip of tearable material that covers or joins a longitudinal slit in the wall. The tearable material may be a polymeric material, an adhesive, paper, film or the like. The protective tube 560', having a rigid structure, acts as a support to hold the capillary tube assembly 100 in alignment with the open distal end of protective tube 560' that is sealed with a detachable seal or disposed with intermediate coupling 520.

Where the intermediate coupling 520 is present, the protective tube 560' also covers at least part of the intermediate coupling 520, preferably part of its proximal end. The protective tube 560' further acts as a support to hold the capillary tube assembly 100 in temporary (dismountable) fixed relation to the intermediate coupling 520. The capillary tube assembly 100 and the intermediate coupling 520 are supported by the protective tube 560' such that the capillary tube shaft 10 is located within the body of the intermediate coupling 520. More in particular, in a non-deployed condition, the distal 30 tip of the capillary tube shaft 10 is located within the body of the intermediate coupling 520, preferably within the opening of the proximal coupling 522, distal coupling 524, or within the chamber 526. Preferably, the distal tip of the capillary tube shaft 10 does not protrude from the distal coupling 524 of the intermediate coupling 520.

The intermediate coupling 520 is dismountably attached to the distal 30 end of the protective tube 560'. Preferably, the intermediate coupling 520 is dismountably attached to the opening at the distal end 30 of the protective tube 560'. Preferably, the dismountable attachment allows the intermediate coupling 520 to rotate relative to the protective tube 560'. The axis of rotation is preferably co-axial with the central axis of the intermediate coupling 520 and/or with the central axis of the protective tube 560'. Preferably, the dismountable attachment prevents the intermediate coupling 520 from translation relative to the protective tube 560'. The dismountable attachment may utilise a frictional joint owing to a close fit of the intermediate coupling at the distal end of the protective tube. The dismountable attachment may be in the form of an arrangement of interlocking or intercalating collars or rings (FIG. 13), at least one collar 528, 530 disposed on the intermediate coupling 520 and at least one collar 564 disposed on the inner surface of protective tube. The respective collars 528, 530, 564 engage, restricting longitudinal displacement of intermediate coupling 520 relative to the protective tube 560' while allowing rotation of the intermediate coupling 520 relative to the protective tube 560. In a preferred embodiment, the intermediate coupling 520 is provided with a pair of collars 528, 530, spatially separated in the longitudinal direction; the protective tube 560' is provided with a collar 564 configured to engage or intercalate in the space between the pair of collars of the intermediate coupling 520. Since the attachment is dismountable, the intermediate coupling 520 may be separated from the protective tube 560' by the application of a force in the longitudinal direction, preferably in the distal direction.

The protective tube 560' may contain no intermediate coupling. It may instead contain detachable seal 585 (FIG. 37). Where the detachable seal is present, the protective tube 560', acts as a support to hold the capillary tube assembly 100 in temporary (dismountable) fixed relation to the detachable seal, more in particular to the distal opening in the protective tube 560' formed when the seal 585 is removed. The capillary tube assembly 100 is supported by the protective tube 560' such that the capillary tube shaft 10 is located in a cone-shaped tip of the distal opening. Preferably the protective tube at the distal end 30 comprises a conical or pointed tip which incorporates the detachable seal 585 (FIG. 37). When the seal 585 is removed, the tip retains truncated a conical or pointed portion. The conical or pointed tip allows alignment of protective tube 560' within the coupling 240 of the invasive tube 200. The seal 585 may be removed by means of a weakened joint 586, or can be removed by cutting.

Figure 14:
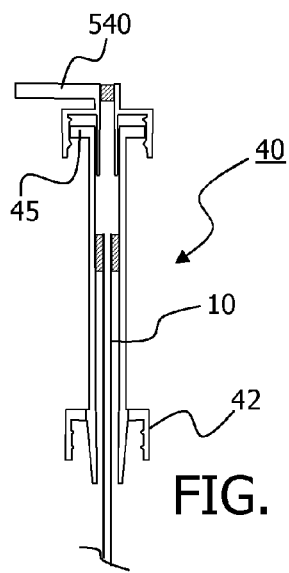
FIG. 14 depicts a cross-sectional view in a plane parallel to the longitudinal direction of part of a capillary tube assembly devoid of a side port and provided with a dismountable handle.
Figures 20, 21, 22:
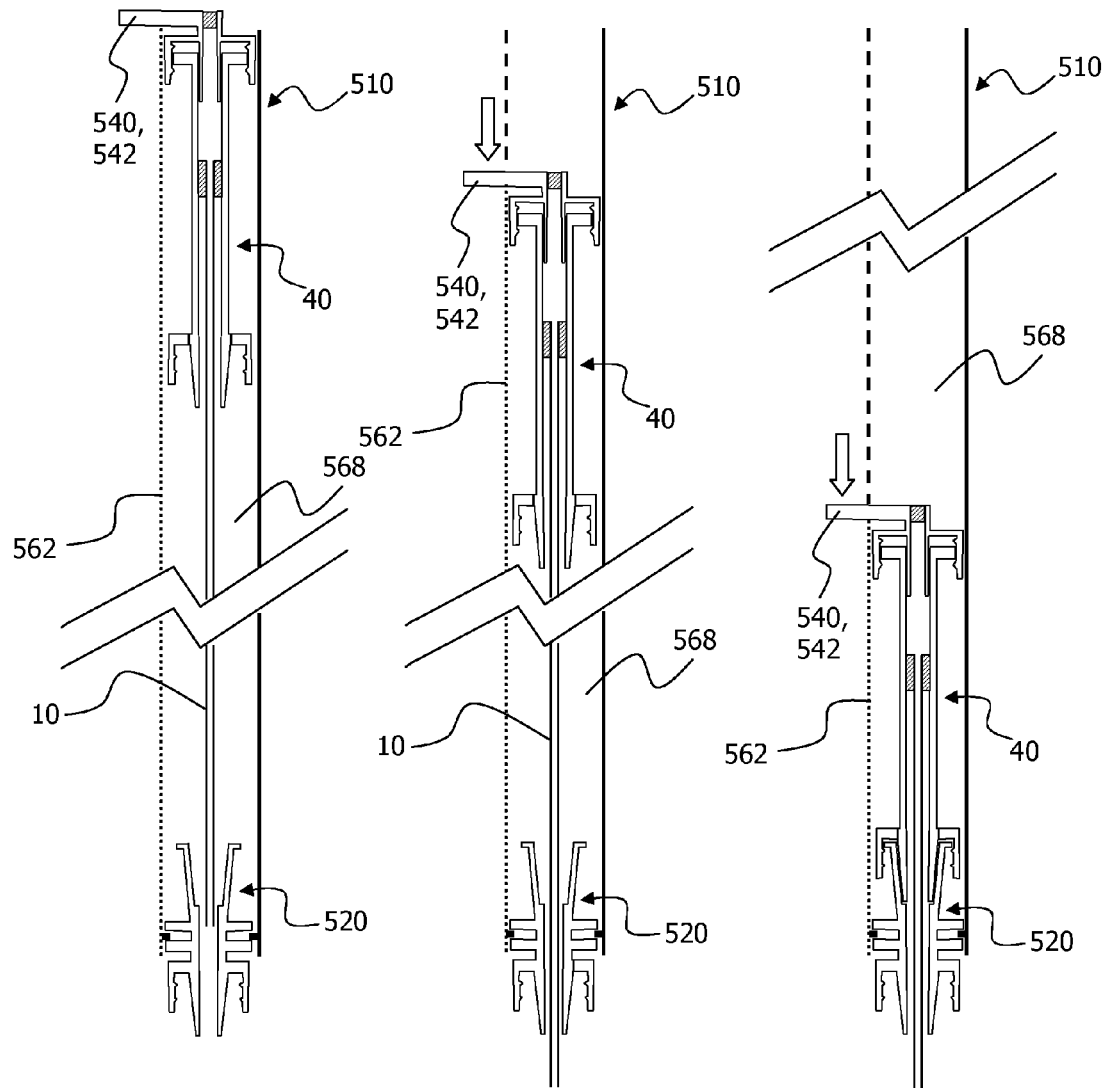
FIGS. 20 to 22 depict a cross-sectional view in a plane parallel to the longitudinal direction of an applicator package of the invention that comprises a protective rigid tube; it shows the stages of advancing the capillary tube assembly within an applicator of the invention, wherein handle is formed from a handle member dismountably attached to the catheter tube assembly adapter.

As mentioned earlier, the capillary tube assembly 100 is disposed in slidable relation to the distal opening in the protective tube 560', more in particular in slidable relation to the intermediate coupling 520 or opening formed from the detached seal 585. The capillary tube assembly 100 is provided with a handle 540 by which it can be slid longitudinally within the protective tube. The handle 540 is configured to breach the longitudinal breachable seal 562 as it slides towards the distal opening in the protective tube 560' e.g. towards the proximal end of the intermediate coupling 520. The handle 540 is preferably attached to the adapter 40 of the capillary tube assembly 100. The handle 540 may be the side port 49 of the adapter 40 as shown in FIG. 13. The handle 540 may be a handle member 542 dismountably attached to the adapter 40, for example, to the proximal port of the adapter 40 as shown in FIG. 14. The movements of the adapter 40 of the capillary tube assembly 100 are depicted in FIGS. 17 to 19, when the handle 540 is the side port 49, and in FIGS. 20 to 22 when the handle 540 is a detachable handle member 542. FIGS. 17 and 20 show the adapter 40 in a non-deployed position. FIGS. 18 and 21 show the adapter 40 advanced towards the distal end, using the handle 540 (side port 49 in FIG. 18 or detachable handle member 542 in FIG. 21). FIGS. 19 and 22 show the adapter 40 fully advanced towards the distal end, and connected to the intermediate coupling 520.

An exemplary configurations of an applicator package 500, is provided in FIGS. 25 to 29. FIG. 25 shows a perspective view of an assembled applicator package having a protective tube 560', breachable seal 562, intermediate coupling 520, and showing the side port 49 of the adapter of the capillary tube assembly. FIG. 26 shows a perspective view of a disassembled applicator package having a protective tube 560', breachable seal 562, intermediate coupling 520, and capillary tube assembly 100 comprising a side port 49 and shaft 10. FIG. 27 shows a perspective view of an assembled applicator package in which the protective tube is removed to highlight the relation of the intermediate coupling 520 to the capillary tube shaft 10. FIG. 28 shows a cross-sectional view of the intermediate coupling 520 and capillary tube assembly 100, where the latter is disposed with a single lumen. FIG. 29 shows a cross-sectional view of the intermediate coupling 520 and capillary tube assembly 100, where the latter is disposed with a double lumen.

A possible sequence of steps for inserting the shaft 10 of the capillary tube assembly 100 into an invasive tube 200 is depicted in FIGS. 30 to 33. The practitioner connects the intermediate coupling 520 to the coupling 240 of the invasive tube 200 (FIGS. 30 and 31). It is noted that the capillary tube shaft 10 is packaged already disposed within the intermediate coupling 520. Using the handle 540 (i.e. side port 40) of the adapter 40 of the capillary tube assembly 100, the adapter 40 is advanced towards the distal end 30 of the protective tube 560'. In doing so, the longitudinal breachable seal 562 is breached. Once at the distal end of the protective tube (FIG. 32), the adapter 40 is connected to the intermediate coupling 520 by rotation of the protective tube 560'. During the longitudinal transit of the adapter 40, the capillary tube shaft 10 is concomitantly inserted into the lumen 212 of the invasive tube 200. It is noted that the step of insertion and coupling to the adapter 40 of the capillary tube assembly 100 take place within the confines of the protective tube 560 which provides a sterile environment. After the intermediate coupling 520 has been connected at both ends, the protective tube is removed (FIG. 33).

According to one aspect of the invention, the protective tube 560', is provided with one or more longitudinal compliant barbs (602, 204) attached to the inside wall of the protective tube 560". With reference to FIG. 43, a barb comprises a longitudinal member 606 that is compliant i.e. it can deform upon the application of force, attached at one end (base end) to the inside wall of the protective tube 560", and optionally having at the other end (tip end) a notch 608 for receiving the capillary tube shaft 10. The compliant member may have spring property. The barbs may be arranged in diametrically opposing pairs on the inside of the protective tube 560' as shown in FIGS. 39 to 42. When arranged in pairs, at least one, preferably both of the pairs contain the notch 608 at the tip. The paired barbs together form an orifice 610 through which the capillary tube shaft 10 passes and can be supported (FIG. 39A) in the protective tube 560'; this is advantageous when the capillary tube shaft 10 is particularly narrow and hence flexible; the barbs can provide the capillary tube shaft with additional pushability. As the adapter 40 advances distally along the protective tube 560' a force is applied to the barbs as they contact the distal end of the adapter 40. The force pushes the complaint barbs 602, 204 away from the path of the adapter 40, allowing the adapter 40 to advance relatively unhindered (FIGS. 40, 41). When the distal end of the adapter 40 has passed a barb 602, 204 (FIG. 42), the barb's compliant property may warrant a full or partial return of the barb to its original position. The barbs may be disposed inclined to a longitudinal axis of the protective tube 560'. The tip of each barb is preferably oriented in the distal 30 direction. A barb may be formed from the wall of the protective tube 560' for example, by cutting out a barb pattern and folding it into the protective tube 560' until the desired position (e.g. inclined) is met. The pattern may be cut using know techniques, for example, a laser or water jet.

The applicator package 500 comprising a protective tube may be provided in a sterile outer packaging. The sterile outer packaging allows storage of a sterilized applicator package 500 without additional contamination from micro-organisms. Preferably, the sterile outer packaging allows the passage of ionising radiation or ETO for sterilization of the applicator package 500 after packaging. The sterile packaging may take the form of a tub or bag provided with a peelable lid.

According to another embodiment of the invention, the protective cover 560 is a flexible pouch 560" that covers at least partially the capillary tube assembly 100 (FIGS. 34, 35). The pouch 560" has a longitudinal shape, and is provided with an interior void 568. The pouch 560" may have an open distal end. The opening at the distal end 30 may be sealed with a detachable seal 585' (FIG. 38) or with an intermediate coupling 520 (FIG. 34, 35). The pouch 560" may have an open or closed proximal end. The flexible pouch 560", acts as a support to hold the capillary tube assembly 100 in temporary (dismountable) fixed relation to the opening at the distal end of the flexible pouch 560". The capillary tube assembly 100 may be slidably mounted in the void 568. Since the pouch is flexible, the capillary tube shaft 10 can be manipulated within the pouch. Moreover, the pouch can buckle thereby adapting shape while the capillary tube shaft 10 is advanced.

Where the intermediate coupling 520 is present (FIGS. 34, 35), the flexible pouch 560" that covers at least partially the intermediate coupling 520 (FIGS. 34, 35), preferably part of its proximal end. The capillary tube assembly 100 and the intermediate coupling 520 are supported by the flexible pouch 560" such that the capillary tube shaft 10 is located within the body of the intermediate coupling 520. More in particular, in a non-deployed condition, the distal 30 tip of the capillary tube shaft 10 is located within the body of the intermediate coupling 520, preferably within the opening of the proximal coupling 522, distal coupling 524, or within the chamber 526. Preferably, the distal tip of the capillary tube shaft 10 does not protrude from the distal coupling 524 of the intermediate coupling 520.

Where the detachable seal 585' is present (FIG. 38), the flexible pouch 560" acts as a support to hold the capillary tube assembly 100 in temporary (dismountable) fixed relation to the detachable seal 585', more in particular to the opening formed by the removal of the detachable seal 585'. The capillary tube assembly 100 is supported by the flexible pouch 560" such that the capillary tube shaft 10 is located in a cone-shaped tip of the distal opening.

The adapter 40 at the proximal 20 end may be enclosed by the flexible pouch 560" (FIG. 34). Alternatively, the connector 45 at the proximal end of the adapter 40, and/or the side port 49 of the adapter 40 may protrude from the flexible pouch 560" (FIG. 35). The adapter 40 may be dismountably attached to the proximal 20 end of the flexible pouch 560". The adapter 40 may not be attached, dismountably or otherwise, to the proximal 20 end of the flexible pouch 560".

The pouch may be made from any flexible material having the requisite sterile-maintaining properties, sealable, and has low leeching and low toxicity. It is preferably made from a transparent material. Typically, it is made from a polymer such as polyethylene or polypropylene. It may be made of laminated foil or paper.

The capillary tube shaft 10 of the capillary tube assembly 100 may be advanced distally through the open distal end by sliding the adapter 40 in a distal direction. The capillary tube shaft 10 advances through the intermediate coupling 520 at the distal open end, or through the opening at the distal end detached from the detachable seal. In particular, the capillary tube assembly 100 may be deployed by tactile pinching of both the flexible pouch and capillary tube shaft 10 and advancing both distally. The flexible pouch 560" buckles and collapses distal of the pinch point, while the capillary tube shaft 10 advances through the open distal end. After advancement by a certain amount, the pouch can be straightened out (i.e. buckles removed by pulling the pouch straight longitudinally) relative to the capillary tube shaft 10, and advancement repeated at the same or different pinch point until the capillary tube shaft 10 has entered the invasive tube. This particularly applies where the adapter 40 is not attached to the flexible pouch 560" i.e. the adapter 40 can slide relative to the flexible pouch 560" (e.g. FIG. 34).

Alternatively, the adapter 40 may be advanced relative to the flexible pouch 560" by tactile pinching of the flexible pouch just proximal to the adapter 40 thereby applying a distal force behind the assembly 100 which advances it 100 forwards (distally) within the pouch void 568. This particularly applies where the adapter 40 is not attached to the flexible pouch 560" i.e. the adapter 40 can slide relative to the flexible pouch 560" (e.g. FIG. 34).

Alternatively, the capillary tube assembly 100 may be deployed by tactile pinching of both the flexible pouch 560" and adapter 40 and advancing both distally. The flexible pouch 560" buckles and collapses distal of the pinch point, while the capillary tube shaft 10 advances into the intermediate coupling 520. After advancement by a certain amount, the pouch can be straightened out (i.e. buckles removed by pulling the pouch straight longitudinally) relative to the capillary tube shaft 10, and advancement repeated at the same or different pinch point until the capillary tube shaft 10 has entered the invasive tube. This particularly applies where the adapter 40 is not attached to the flexible pouch 560" i.e. the adapter 40 can slide relative to the flexible pouch 560" (e.g. FIG. 34).

Alternatively, the capillary tube assembly 100 may be deployed by holding the adapter 40 and advancing it distally. This particularly applies where the adapter 40 is dismountably attached to the flexible pouch 560" (e.g. FIG. 35).

The intermediate coupling 520 where present is dismountably attached to the distal 30 end of the flexible pouch 560" (FIG. 34, 35). Preferably, the intermediate coupling 520 is dismountably attached to the opening at the distal end 30 of the flexible pouch 560". Preferably, the dismountable attachment allows the intermediate coupling 520 to rotate relative to the flexible pouch 560". The dismountable attachment may utilise a frictional joint owing to a close fit of the intermediate coupling at the distal end of the flexible pouch 560". The dismountable attachment may be in the form of an arrangement of interlocking or intercalating collars or rings (FIGS. 34, 35), at least one collar 528, 530 disposed on the intermediate coupling 520 and at least one collar 564" disposed on the inner surface or outer surface of flexible pouch 560". The respective collars 528, 530, 564 engage, acting as stops, restricting longitudinal displacement of intermediate coupling 520 relative to the flexible pouch 560" while allowing rotation of the intermediate coupling 520 relative to the flexible pouch 560". It will be appreciated that the respective collars 528, 530, 564 may engage directly when the collar is disposed on the inner surface of flexible pouch 560", or they may engage through the material of the pouch 560" when the collar is disposed on the outer surface of flexible pouch 560". In a preferred embodiment, the intermediate coupling 520 is provided with a pair of collars 528, 530, spatially separated in the longitudinal direction; the flexible pouch 560" is provided with an outer collar 564" configured to engage or intercalate in the space between the pair of collars of the intermediate coupling 520. Since the attachment is dismountable, the intermediate coupling 520 may be separated from the flexible pouch 560" for example by the application of a force in the longitudinal direction, preferably in the distal direction. Other dismountable means are envisaged, including a pull tab on the flexible pouch 560" which breaks the collar 564".

The flexible pouch 560" may contain no intermediate coupling. It may instead contain detachable seal. Where the detachable seal 585' is present (FIG. 38), the distal end of the flexible pouch may have a conical or pointed tip 586' which incorporates the detachable seal. When the seal is removed, the tip retains truncated a conical or pointed portion. The conical or pointed tip allows alignment of the distal end of the flexible pouch 560" within the coupling 240 of the invasive tube 200. The seal 585' may be removed by means of a weakened joint 586', or can be removed by cutting. It is to be understood that the detachable seal at the distal end of the flexible pouch 560" provides an alternative means to guide the capillary tube shaft 10 into the invasive tube 200; it is not excluded that the intermediate coupling is covered by a tearable seal for maintaining sterility.

The adapter 40 may not be attached to the flexible pouch 560". According to one embodiment, the adapter 40 may be dismountably attached to the proximal 20 end of the flexible pouch 560". Preferably, the adapter 40 may be dismountably attached to an opening at the proximal end 20 of the flexible pouch 560". The dismountable attachment may utilise a frictional attachment owing to a close fit of the adapter 40 at the proximal end of the flexible pouch 560". In particular the frictional attachment may be located between the connector 45 at the proximal end of the adapter 40 and the side port 49 of the adapter 40 (FIG. 35). Alternatively, the frictional attachment may be located between the side port 49 of the adapter 40 and the open connector 42 at the distal end of the adapter 40 (not shown). The frictional attachment may be in the form of a collar or ring 566 disposed on the inner or outer surface of flexible pouch 560" at the proximal end which creates a frictional engagement with the outer surface of the adapter 40. The pouch, or more particularly, the opening, frictionally engages with the adapter 40, restricting longitudinal displacement of adapter 40 relative to the flexible pouch 560". Since the attachment is dismountable, the adapter 40 may be separated from the flexible pouch 560", for example, by the application of a force in the longitudinal direction, preferably in the distal direction. Other dismountable means are envisaged, including a pull tab on the flexible pouch 560" which breaks the collar 566.

The applicator package 500 comprising a flexible pouch may be provided in a rigid outer packaging, such as a rigid hollow tube. The rigid outer packaging allows storage of an applicator package 500 without damage to the capillary tube. The rigid outer packaging may allows the passage of ionising radiation or ETO for sterilization of the applicator package 500 in the outer packaging.

According to another embodiment of the invention, the protective cover 560 is a hollow bellows tube 560''' (FIG. 36) that covers at least partially the capillary tube assembly 100. The bellows tube 560''' is longitudinal, and provided with an interior void 568. The bellows tube 560''' may have an open distal end. The opening at the distal end 30 may be sealed with a detachable seal or with an intermediate coupling 529. The bellows tube 560''' may have an open or closed proximal end. At least part of the bellows tube 560''' is bellowed i.e. is a concertina tube, enabling it to collapse in the longitudinal direction; thus it can guide the capillary tube shaft 10 forward as the tube collapses. Preferably, the distal and proximal tips of the bellows tube 560''' are not bellowed to facilitate attachment to the adapter 40, or intermediate coupling 520, or detachable seal.

Where the intermediate coupling 520 is present, the hollow bellows tube 560''' (FIG. 36) covers at least partially the intermediate coupling 520, preferably part of the proximal end of the intermediate coupling 520. The bellows tube 560''' acts as a support to hold the capillary tube assembly 100 in temporary (dismountable) fixed relation to the intermediate coupling 520. The capillary tube assembly 100 is slidably mounted in the void 568. The capillary tube assembly 100 and the intermediate coupling 520 are supported by the bellows tube 560''' such that the capillary tube shaft 10 is located within the body of the intermediate coupling 520. More in particular, in a non-deployed condition, the distal 30 tip of the capillary tube shaft 10 is located within the body of the intermediate coupling 520, preferably within the opening of the proximal coupling 522, distal coupling 524, or within the chamber 526. Preferably, the distal tip of the capillary tube shaft 10 does not protrude from the distal coupling 524 of the intermediate coupling 520. The side port 49 of the adapter 40 may protrude from the bellows tube 560''' (FIG. 36). The adapter 40 may be dismountably attached to the proximal 20 end of the bellows tube 560'''. The adapter 40 may not be attached, dismountably or otherwise, to the proximal 20 end of the bellows tube 560".

The intermediate coupling 520 is dismountably attached to the distal 30 end of the bellows tube 560'''. Preferably, the intermediate coupling 520 is dismountably attached to an opening at the distal end 30 of the bellows tube 560'''. Preferably, the dismountable attachment allows the intermediate coupling 520 to rotate relative to the bellows tube 560'''. The axis of rotation is preferably co-axial with the central axis of the intermediate coupling 520 and/or with the central axis of the bellows tube 560'''. Preferably, the dismountable attachment prevents the intermediate coupling 520 from translation relative to the bellows tube 560'''. The dismountable attachment may utilise a frictional joint owing to a close fit of the intermediate coupling at the distal end of the protective tube. The dismountable attachment may be in the form of an arrangement of interlocking or intercalating collars or rings (FIG. 36), at least one collar 528, 530 disposed on the intermediate coupling 520 and at least one collar 564''' disposed on the inner surface of bellows tube 560'''. The respective collars 528, 530, 564''' engage, restricting longitudinal displacement of intermediate coupling 520 relative to the bellows tube 560''' while allowing rotation of the intermediate coupling 520 relative to the bellows tube 560'''. In a preferred embodiment, the intermediate coupling 520 is provided with a pair of collars 528, 530, spatially spaced in the longitudinal direction; the bellows tube 560''' is provided with a collar 564''' configured to engage or intercalate in the space between the pair of collars of the intermediate coupling 520. Since the attachment is dismountable, the intermediate coupling 520 may be separated from the bellows tube 560''' by the application of a force in the longitudinal direction, preferably in the distal direction.

The bellows tube 560''' may contain no intermediate coupling. It may instead contain detachable seal. Where the detachable seal is present, the bellows tube 560''' acts as a support to hold the capillary tube assembly 100 in temporary (dismountable) fixed relation to the detachable seal. The capillary tube assembly 100 is supported by the bellows tube 560''' such that the capillary tube shaft 10 is located in a cone-shaped tip of the distal opening. The distal end of the bellows tube 560''' may have a conical or pointed tip which incorporates the detachable seal. When the seal is removed, the tip retains truncated a conical or pointed portion. The conical or pointed tip allows alignment of the distal end of the bellows tube 560''' within the coupling 240 of the invasive tube 200.

The bellows tube 560''' may be made from any material having the requisite sterile-maintaining properties, sealable, and low leeching, and low toxicity. It is preferably made from a transparent material. Typically, it is made from a polymer such as polypropylene.

According to one embodiment, the adapter 40 may be dismountably attached to the proximal 20 end of the bellows tube 560'''. Preferably, the adapter 40 may be dismountably attached to an opening at the proximal end 20 of the bellows tube 560'''. The dismountable attachment may utilise an opening 570 in the side wall of the bellows tube 560''' through which the side port 49 of the adapter 40 is disposed or through which a handle member dismountably attached to the adapter (40) is disposed and engaged. Thus, the adapter 40 is advanced in the distal 30 direction when the bellows tube 560''' is collapsed. Since the attachment is dismountable, the adapter 40 may be separated from the bellows tube 560''', for example, by dismounting the side port 49 or handle of the adapter 40 from the opening 570.

The applicator package 500 comprising a bellows tube may be provided in a sterile outer packaging. The sterile outer packaging allows storage of a sterilized applicator package 500 without additional contamination from micro-organisms. Preferably, the sterile outer packaging allows the passage of ionising radiation or ETO for sterilization of the applicator package 500 after packaging. The sterile packaging may take the form of a tub or bag provided with a peelable lid.

The kits below may be provided with the capillary tube assembly 100 provided as part of an applicator package 500.

One aspect of the invention provides a kit comprising:
a capillary tube assembly 100 as described herein, and
an invasive tube 200 as described herein.
One aspect of the invention provides a kit comprising:
an applicator package 500 as described herein, and
an invasive tube 200 as described herein.
One aspect of the invention provides a kit comprising:
an applicator package 500 as described herein.

Preferably, the invasive tube 200 is a catheter or a lumbar puncture needle.

The kit may further comprise a pressure gauge suitable for connection to the adapter at the proximal end of the capillary tube assembly.

The uses below may be performed with the capillary tube assembly 100 provided as part of an applicator package 500.

One aspect of the invention is a use of a kit as described herein for measurement of hydrostatic pressure in a cavity.

Another aspect of the invention is a use of capillary tube assembly 100 as described herein for reversibly adapting a catheter with an additional lumen.

The method below may be performed with the capillary tube assembly 100 provided as part of an applicator package 500.

One aspect of the invention is a method for measurement of hydrostatic pressure in a cavity comprising the steps:
inserting the distal end of an invasive tube 200 as described herein into the cavity,
inserting a capillary tube assembly 100 into a lumen 212 of an invasive tube 200,
connecting a distal end of the adapter 40 of the capillary tube assembly 100 to the coupling 240 of the invasive tube 200,
providing incompressible fluid to the lumen of the capillary tube assembly 100,
connecting the proximal end of the adapter 40 of the capillary tube assembly 100 to a pressure gauge
thereby measuring the hydrostatic pressure in the cavity.
Preferably, the invasive tube 200 is a lumbar puncture needle 200'''.

One aspect of the invention is a method for adapting an existing catheter 200' to provide an additional lumen, said catheter provided with at least one catheter lumen 212' extending between an open distal 30 end and an open proximal 20 end for conductance of a fluid, and a coupling 240' at the proximal 20 end in fluid connection with said catheter lumen 212', comprising the steps:
inserting the distal 30 end of a capillary tube assembly 100 as described herein into the lumen 212' of the catheter through its open proximal 20 end,
connecting a distal 30 end of the adapter 40 of the capillary tube assembly 100 to the coupling 240' of the catheter 200', wherein said adapter is preferably a Y-shaped hub, thereby providing the catheter 200' with an additional lumen which is the capillary tube lumen 12.

The invention claimed is:

1. A kit comprising:
a bodily invasive tube that is a venous catheter, and
a detachable device for adding one or more channels to the bodily invasive tube which detachable device comprises a capillary tube assembly having a proximal end and a distal end and comprises:
a thin walled capillary tube shaft disposed with a capillary lumen extending from an open proximal end to an open distal end, and
a fluidic adapter at the proximal end in fluid connection the capillary tube lumen,
wherein
the capillary tube shaft is adapted for dismountable insertion into a fluid-carrying lumen of the bodily invasive tube that is the venous catheter, such that the distal tip of the capillary tube protrudes from the distal tip of the bodily invasive tube, and to maintains the flow function of the venous catheter,
the adapter is configured to provide fluidic access to the capillary tube lumen that is fluidically isolated from access to the invasive tube lumen, and an applicator wherein the detachable device is packaged in the applicator, said applicator comprising:
a longitudinal protective cover having a proximal end and a distal end,
an opening at the distal end,
wherein
the protective cover forms a void in which the capillary tube shaft and at least a distal part of the adapter are disposed, and
the cover is configured such that the capillary tube shaft is slidable relative to the opening at the distal end,
wherein an intermediate coupling is dismountably attached through the opening at the open distal end of the applicator cover, which coupling has a proximal and distal end, a fluidic coupling at the proximal end of the intermediate coupling configured for attachment to the adapter of the capillary tube assembly and a fluidic coupling at the distal end of the intermediate coupling configured for attachment to a coupling on the invasive tube, both fluidic couplings of the intermediate coupling joined to an internal chamber,
wherein
at least a proximal part of the intermediate coupling is deposed in the void of the protective cover, and
the distal end of the capillary tube shaft is positioned for passage through the fluidic coupling at the proximal end of the intermediate coupling.

2. The kit according to claim 1 wherein
the adapter is configured for dismountable connection to a coupling on the invasive tube,
the invasive tube to which the capillary tube assembly can be dismountably inserted comprises:
a hollow longitudinal shaft having a proximal end and a distal end, disposed with an invasive tube lumen extending from an open proximal end to an open distal end, and
a coupling at the proximal end in fluid connection with the invasive tube lumen, and
the hollow longitudinal shaft is configured for introduction into a bodily lumen from its distal end.

3. The kit according to claim 1, wherein
said adapter has distal end and proximal end,
the distal end of the adapter is provided with a fluidic connector configured for dismountable fluidic connection to the coupling of the invasive tube, the proximal end of the adapter is provided with a fluidic connector in fluid connection with the capillary tube lumen for dismountable fluidic connection to a reciprocating fluidic connector, and the proximal and distal end fluidic connectors are fluidically isolated in the adapter.

4. The kit according to claim 3, wherein said adapter is further provided with a side port in fluid connection with the distal end fluidic connector of the adapter.

5. The kit according to claim 3, wherein the fluidic connector at the distal end of the adapter is provided with a male or female Luer lock connector.

6. The kit according to claim 1, wherein the capillary tube shaft is formed at least partially, preferably entirely from polyimide.

7. The kit according to claim 1, wherein the capillary tube has a wall thickness of 0.02 mm to 0.13 mm.

8. The kit according to claim 1, wherein the venous catheter is configured for insertion through a jugular vein.

9. The kit according to claim 1, wherein the distal tip of the capillary tube shaft protrudes relative to the distal tip of the invasive tube by 0.1 mm to 10 mm.

10. The kit according to claim 1, wherein the venous catheter is a central venous catheter.

11. The kit according to claim 1, wherein the opening at the distal end of the longitudinal protective cover of the applicator is sealed with a detachable seal.

12. The kit according to claim 1, wherein:
the protective cover is comprised of a rigid, hollow protective tube having a proximal and distal end, and a breachable seal disposed along the longitudinal length of the wall of the tube, and the breachable seal is configured to breach as the adapter is slidably advanced towards the intermediate coupling.

13. The kit according to claim 12, wherein the adapter is dismountably attached to the protective tube using a handle attached to the adapter that protrudes through the breachable seal of the protective tube.

14. The kit according to claim 13, wherein said handle is:
a side port attached to the adapter in fluid connection with the distal end fluidic connector of the adapter, or a handle member dismountably attached to the adapter.

15. The kit according to claim 1, wherein the protective cover is comprised of a longitudinal flexible pouch having a proximal and distal end.

16. The kit according to claim 15, wherein the adapter is dismountably attached to the proximal end of the flexible pouch.

17. The kit according to claim 1, wherein the protective cover is comprised of a longitudinal hollow bellows tube having a proximal and distal end, and comprising at least a bellowed portion of tubing.

18. The kit according to claim 17, wherein the adapter is dismountably attached to the proximal end of the bellows tube.

19. The kit according to claim 18, wherein the adapter is dismountably attached to the bellows tube using a handle attached to the adapter that protrudes through a side opening of the bellows tube.

20. The kit according to claim 19, wherein said handle is:
a side port attached to the adapter in fluid connection with the distal end fluidic connector of the adapter, or a handle member dismountably attached to the adapter.

21. The kit according to claim 1, when said capillary tube shaft is disposed with more than one capillary lumens extending from an open proximal end to an open distal end, and a separate fluidic adapter at the proximal end is in fluid connection with each capillary tube lumen.

22. The kit according to claim 1, wherein
the venous catheter into which the capillary tube assembly can be dismountably inserted comprises a hollow longitudinal shaft having an open proximal end and an open distal end, and said hollow longitudinal shaft comprises one or more venous catheter lumens extending from an open proximal end to an open distal end, and a separate fluidic coupling at the proximal end is in fluid connection with each invasive tube lumen.

* * * * *

UNITED STATES PATENT AND TRADEMARK OFFICE
CERTIFICATE OF CORRECTION

PATENT NO. : 8,882,716 B2  
APPLICATION NO. : 13/810427  
DATED : November 11, 2014  
INVENTOR(S) : Frank Dewaele et al.

Page 1 of 1

It is certified that error appears in the above-identified patent and that said Letters Patent is hereby corrected as shown below:

Title Page (item 57, Abstract) at line 3, Change "think" to --thin--.

Title Page (item 57, Abstract) at lines 7-8, Change "connection the capillary" to --connection with the capillary--.

In the Specification

In column 1 at line 31, Change "hematothorax," to --hemothorax,--.

In column 1 at lines 47-48, Change "nocturesis." to --nocturia.--.

In column 2 at line 19, Change "catheter" to --catheter.--.

In column 2 at line 26, Change "the" to --with the--.

In column 3 at line 37 (approx.), Change "(520)" to --(520).--.

In column 4 at line 11 (approx.), Change "(560)," to --(560).--.

In column 8 at line 5, After "any" insert --$\geq 3, \geq 4, \geq 5, \geq 6$ or $\geq 7$-- --.

In column 10 at lines 25-26, Change "Tersons's" to --Terson's--.

In column 11 at line 66, Change "hematothorax," to --hemothorax,--.

In column 20 at line 62, Change "fludic" to --fluidic--.

In column 27 at line 33, Change "allows" to --allow--.

In the Claims

In column 30 at line 13 (approx.), In Claim 1, change "the capillary" to --with the capillary--.

Signed and Sealed this  
Seventh Day of July, 2015

Michelle K. Lee  
*Director of the United States Patent and Trademark Office*